(12) United States Patent
Tiganescu et al.

(10) Patent No.: US 11,590,119 B2
(45) Date of Patent: Feb. 28, 2023

(54) (S)-2-(1-(5-(CYCLOHEXYLCARBAMOYL)-6-(PROPYLTHIO)PYRIDIN-2-YL)PIPERIDIN-3-YL)ACETIC ACID FOR USE IN MEDICINE

(71) Applicant: University of Leeds, Leeds (GB)

(72) Inventors: Ana Tiganescu, Leeds (GB); Paul Stewart, Leeds (GB)

(73) Assignee: University of Leeds, Leeds (GB)

( * ) Notice: Subject to any disclaimer, the term of this patent is extended or adjusted under 35 U.S.C. 154(b) by 150 days.

(21) Appl. No.: 17/095,424

(22) Filed: Nov. 11, 2020

(65) Prior Publication Data

US 2021/0137912 A1    May 13, 2021

(30) Foreign Application Priority Data

Nov. 12, 2019   (EP) .................................. 19208698

(51) Int. Cl.
| | | |
|---|---|---|
| *A61K 31/4545* | (2006.01) | |
| *A61P 17/02* | (2006.01) | |
| *A61K 9/00* | (2006.01) | |
| *A61K 31/573* | (2006.01) | |
| *A61K 45/06* | (2006.01) | |

(52) U.S. Cl.
CPC ........ *A61K 31/4545* (2013.01); *A61K 9/0053* (2013.01); *A61K 31/573* (2013.01); *A61K 45/06* (2013.01); *A61P 17/02* (2018.01)

(58) Field of Classification Search
CPC ................................................. A61K 31/4545
See application file for complete search history.

(56) References Cited

U.S. PATENT DOCUMENTS 8,673,938 B2 * 3/2014 McCoull ................... A61P 3/06
564/194

FOREIGN PATENT DOCUMENTS

| WO | 2004/112785 A1 | 12/2004 |
| WO | 2017/025989 A1 | 2/2017 |

OTHER PUBLICATIONS

Scott et al. CAS: 157: 184503, 2012.*
International Search Report and Written Opinion dated Jan. 11, 2021 from International Application No. PCT/EP2020/081788.
Ajjan et al., "From bench to bedside and beyond: a novel therapy to improve wound healing in type 2 diabetes EC1.2", Endocrine Abstracts, Nov. 11, 2019 (Nov. 11, 2019), pp. 1-4.
Anonymous, "Glucocorticoids and Skin Healing in Diabetes (GC-SHealD)", ClinicalTrials.gov, Mar. 22, 2019 (Mar. 22, 2019), pp. 1-8.
Armstrong et al., "Validation of a Diabetic Wound Classification System", Diabetes Care, May 1998, vol. 21, No. 5, pp. 855-859.
Freude et al, "Safety, pharmacokinetics and pharmacodynamics of BI 135585, a selective 11 β-hydroxysteroid dehydrogenase-1 (HSD1) inhibitor in humans: liver and adipose tissue 11 β-HSD1 inhibition after acute and multiple administrations over 2 weeks" Diabetes, Obesity and Metabolism, May 2016, vol. 18, No. 5, pp. 483-490.
Lan et al, Diabetes, "High-Glucose Environment Enhanced Oxidative Stress and Increased Interleukin-8 Secretion From Keratinocytes", Diabetes, Jul. 2013, vol. 62, pp. 2530-2538.
Larouche et al., "Immune Regulation of Skin Wound Healing: Mechanisms and Novel Therapeutic Targets" Advances in Wound Care, 2018, vol. 7(7), pp. 209-231.
Mizra et al, "Blocking Interleukin-1b Induces a Healing-Associated Wound Macrophage Phenotype and Improves Healing in Type 2 Diabetes", Diabetes, Jul. 2013, vol. 62, pp. 2579-2587.
National Institute for Health and Care Excellence (NICE) Guideline, Diabetic foot problems: prevention and management; Aug. 2015.
Scott et al., "Medicinal Chemistry of Inhibitors of 11B-Hydroxyseroid Dehydrogenase Type 1 (11b-HSD1)"; Journal of Medicinal Chemistry, 2014, 57, pp. 4466-4486.
Sjöstrand et al, "Pharmacodynamic Effects of AZD4017, a Selective 11beta-HSD1 Inhibitor, in Liver and Adipose Tissue", DiabetesPro, 2011, pp. 1-2.
Small et al., "Preventing local regeneration of glucocorticoids by 11 β-hydroxysteroid dehydrogenase type 1 enhances angiogenesis", PNAS, Aug. 23, 2005, vol. 102, No. 34, pp. 12165-12170.
Tiganescu et al, "11β-Hydroxysteroid dehydrogenase blockade prevents age-induced skin structure and function defects", The Journal of Clinical Investigation, Jul. 2013, vol. 123, No. 7, pp. 3051-3060.
Tiganescu et al, "Topical 11[beta]-Hydroxysteroid Dehydrogenase Type 1 Inhibition Corrects Cutaneous Features of Systemic Glucocorticoid Excess in Female Mice", Endocrinology, Oct. 26, 2017 (Oct. 26, 2017), pp. 1-11.

* cited by examiner

*Primary Examiner* — Rei Tsang Shiao

(57) ABSTRACT

The present specification relates to (S)-2-(1-(5-(cyclohexylcarbamoyl)-6-(propylthio)pyridin-2-yl)piperidin-3-yl)acetic acid (AZD4017), or a pharmaceutically acceptable salt thereof, for oral use in the treatment or prophylaxis of wounds, for example in diabetic patients. Methods of treatment and prophylaxis and the use of the compound in the preparation of a medicament for the treatment and prophylaxis of wounds are also provided.

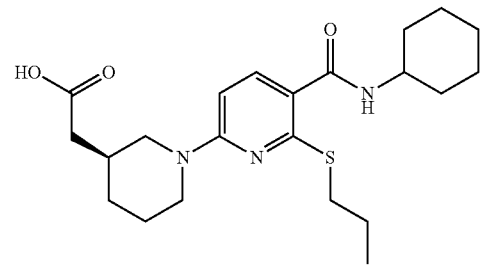

16 Claims, 11 Drawing Sheets

Urinary [THF+alloTHF]/THE ratio: Day 35

PBO mean =1.49

PBO mean =1.38

Figure 1:
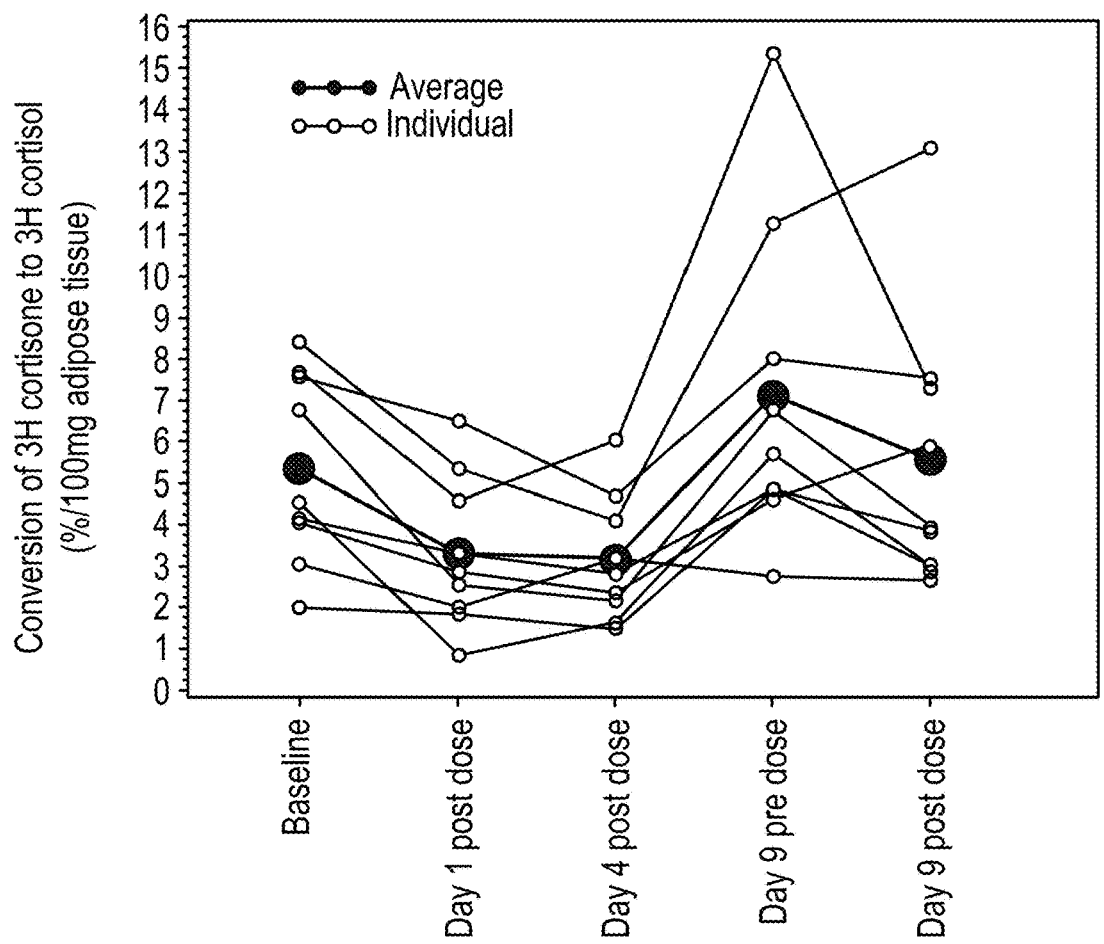

(S)-2-(1-(5-(CYCLOHEXYLCARBAMOYL)-6-(PROPYLTHIO)PYRIDIN-2-YL)PIPERIDIN-3-YL)ACETIC ACID FOR USE IN MEDICINE

CROSS-REFERENCE TO RELATED APPLICATION

This application claims the benefit under 35 U.S.C. § 119(b) and 37 CFR 1.55 of European Application No. 19208698.1 filed Nov. 12, 2019, which is incorporated by reference herein in its entirety for all purposes.

This specification is directed to the oral use of (S)-2-(1-(5-(cyclohexylcarbamoyl)-6-(propylthio)pyridin-2-yl)piperidin-3-yl)acetic acid (AZD4107), a selective 11β-hydroxysteroid dehydrogenase type 1 inhibitor (11β-HSD1 inhibitor), in the treatment or prophylaxis of skin wounds for patients whose ability to heal skin wounds is impaired. Such patients are prone to develop chronic wounds and to suffer from complications arising therefrom. One significant example of a patient population that experience delayed wound healing is the diabetic patient population. The specification also relates to methods of treatment or prophylaxis of patients prone to develop chronic wounds and compounds for use in the manufacture of medicines for the treatment or prophylaxis of chronic wounds, for example for diabetic patients. As described herein, treatment of patients with AZD4017 has been found to improve the rate of wound healing and the skin quality of in patients in need thereof.

In order that the disclosure can be fully appreciated, the specification refers to prior art documents, such reference should not be taken as an acknowledgement that such documents form part of the common general knowledge.

According to a 2010 paper (Senn et al, Wound Repair Regen 2010; 17: 763-771), in 2009 chronic wounds to the skin affected 6.5 million people in the United States and led to $25 billion in annual treatment costs. Rising rates of obesity and diabetes, combined with an aging population, leads to an expectation that the number of people affected by chronic wounds will continue to rise. Ineffective treatment of these wounds can result in infection, sepsis, amputation, and in the most extreme cases, death.

Wound healing is a dynamic, interactive process involving coagulation, inflammation, tissue formation and tissue remodelling. Patients with diabetes mellitus are observed to be more susceptible to infection and other complications during the wound healing process. As a consequence, impaired wound healing is a common cause of morbidity and mortality among diabetes patients. Accordingly, treatment of patients with diabetic wounds, or prophylaxis of this (diabetic) patient population against the development of wounds, is a significant, unmet, clinical need.

There are a number of reasons why wound healing is impaired in diabetic patients, and there is no general successful treatment for promoting wound healing or enhancing its rate in these patients. The high blood sugar levels that are characteristic of diabetes can inhibit the delivery of nutrients and oxygen to skin cells and this in turn can impair the functioning of the immune system and increase inflammation at the cellular level. In addition, high blood sugar levels can damage nerves and vessels, resulting in a numbing of effected tissues (neuropathy). This numbing, or diabetic neuropathy, has been cited as a common cause of injury and complications in diabetic wound healing, with, for instance, a lack of feeling in the feet being associated with unnoticed foot ulcers which are thus allowed to develop unnoticed. Efficient wound healing requires adequate blood supply to the wound site, diabetes is however associated with increased risk of peripheral vascular disease a condition that causes a reduction in the supply of blood circulation to the wound site thus impairing wound healing. The duration of inflammation, a normal part of the wound healing process, is often prolonged in diabetic patients and this can increase the chances of a wound not healing properly leading to development of chronic lesions. Immune cells and immune mediators also play a key role in wound healing and diabetes is associated with a weakening of the immune response, thus compromising wound healing. Impairment of the immune system can also increase the susceptibility of diabetic patients to wound infection, a further factor compromising the rate, and extent of, wound healing.

Glucocorticoids, such as the stress hormone cortisol, cause delayed healing amongst other cutaneous side-effects. In skin, glucocorticoid (GC) excess causes acne, thinning, dryness, atrophic striae, telangiectasia, bruising, impaired wound healing (WH), and increased infection risk. Systemic GC therapy is a mainstream treatment for many inflammatory diseases such as lupus, asthma, chronic obstructive pulmonary disease, inflammatory bowel disease and polymyalgia rheumatica. Skin bruising and thinning have also been reported with low dose (<7.5 mg/d) glucocorticoid therapy. Agents for use in conjunction with GC therapy to improve wound healing could prove to be of great value in the prophylaxis of chronic wounds.

The enzyme 11β-hydroxysteroid dehydrogenase type 1 (11β-HSD1) is a key enzyme on the glucocorticoid biosynthetic pathway that generates cortisol from its inactive precursor (cortisone) in many tissues, including skin, thereby regulating peripheral exposure to glucocorticoids. Although 11β-HSDs have been well-characterized in key metabolic tissues such as adipose, muscle, liver, kidney, brain and bone, their role in modulating skin function in health and disease has not been fully explored to date.

Previous studies from the present inventors revealed increased 11β-HSD1 expression and activity in human and mouse skin and that in mice this can be associated with ageing, wound healing and UVB exposure. Global 11β-HSD1 deletion protected mice from age-associated dermal atrophy and improved expression of collagen biosynthesis and processing enzymes. Furthermore, topical treatment of mice bearing wounds with the non-selective 11β-HSD inhibitor carbenoxolone (CBX) was found to reverse the delay in wound healing caused by corticosteroid excess following oral administration of corticosterone (Tiganescu et al, Endocrinology, 2018, 159(1):547-556). Although the use of a selective 11β-HSD1 inhibitor for wound healing has been proposed in WO2004/112785, no evidence that any positive effect on the rate of wound healing is present in this application or, to the best of our knowledge, elsewhere in the prior art, let alone in human subjects.

Although the studies and hypotheses mentioned above are interesting, prior to the work reported herein no link between 11β-HSD1 inhibition and diabetic wound healing in humans has been established. Indeed, there has been a serious question mark over whether oral administration of 11β-HSD1 inhibitors in humans will provide any benefit on prolonged dosing due to disappointing results obtained when evaluating the therapeutic potential of this class of molecules in the clinic.

The findings that cast serious doubt as to whether oral administration of 11β-HSD1 inhibitors can provide any benefit on prolonged dosing stem from a number of clinical trials in humans wherein 11β-HSD1 inhibitors, including AZD4017, have been shown to initially reduce cortisol level but the effect in adipose tissues was not sustained. In the case of AZD4017, cortisol levels in the adipose tissues after 9 days dosing were actually higher than those measured before dosing commenced (see Sjöstrand M, Hansson G I, Hartford M et al. Pharmacodynamic effects of AZD4017, a selective 11beta-HSD1 inhibitor, in liver and adipose tissue (Abstract 1161-P). *Diabetes* 2011; 60: A319 (available at https://professional.diabetes.org/abstract/pharmacodynamic-effects-azd4017-selective-11beta-hsd1-inhibitor-liver-and-adipose-tissue). Similar findings for BI 135585 are presented in Freude et al: as discussed in more detail below (Safety, pharmacokinetics and pharmacodynamics of BI 135585, a selective 11β-hydroxysteroid dehydrogenase-1 (HSD1) inhibitor in humans: liver and adipose tissue 11β-HSD1 inhibition after acute and multiple administrations over 2 weeks; *Diabetes, Obesity and Metabolism* 18: 483-490, 2016). Accordingly, the suitability of 11β-HSD1 inhibitors for the treatment of chronic conditions in peripheral tissues such as the skin via oral administration, despite extensive clinical evaluation, has not been established and has, indeed seemed unfeasible.

Figure 2:
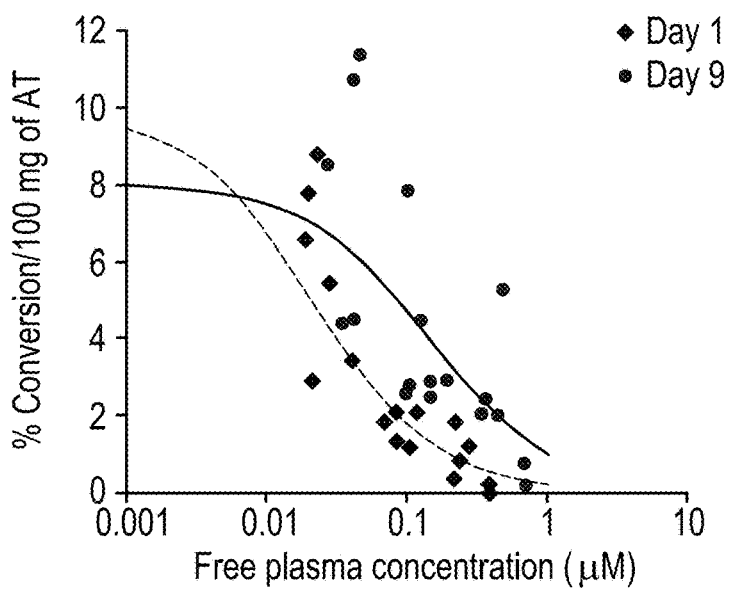

In more detail, a Phase I study using AZD4017 in abdominally obese healthy adult male volunteers involved an assessment of 11β-HSD1 inhibition in human adipose tissue as a function of time following daily oral dosing of the inhibitor (11β-HSD1 activity was assessed by an assay measuring the conversion of cortisone to cortisol in adipose tissue samples). This study revealed that reduced 11β-HSD1 activity relative to baseline could be achieved on day 1 after oral administration of AZD4017 (FIG. 1). Unfortunately, when 11β-HSD1 activity was assessed post dose on day 9, although the 11β-HSD1 activity was reduced after administration of the 11β-HSD1 inhibitor relative to the pre-AZD4017 administration level on day 9, the net 11β-HSD1 activity post-dose on day 9 was still greater than the baseline level on day 0, i.e. prior to commencement of 11β-HSD1 inhibitor administration. A reduction in efficacy for the 11β-HSD1 inhibitor in reducing cortisol level in the adipose tissues over time was thus established (FIG. 1). Tachyphylaxis was also investigated with an additional AstraZeneca 11β-HSD1 inhibitor, AZD8329, from a different chemical series (see Morentin Gutierrez et al, *Br J Pharmacol* 201, 172, 4806-16). Again there was a reduction in efficacy seen in human and rodent samples following repeat dosing relative to that observed after a single (acute) dose, the human data from this study is shown in FIG. 2.

The reduction in efficacy of 11β-HSD1 inhibitors in the adipose compartment following repeat dosing has also been seen with a range of other inhibitors in numerous studies as is discussed in Freude et al. Data in the Freude paper shows that when BI135585 was dosed to human subjects with Type 2 Diabetes at multiple doses there was a significant reduction in efficacy in inhibiting 11β-HSD1 in adipose tissue at 24 h after 14 days of once daily administration of drug compared to that observed at 24 h after administration of a single dose, even at the highest doses of 100 mg and 200 mg used in the study. For example, Freude shows that while the median % 11β-HSD1 inhibition observed in the adipose tissue at 24 h following administration of 200 mg of drug in healthy volunteers was 90%, the median % 11β-HSD1 inhibition in Type 2 Diabetes patients 24 h after 14 days of drug (BI135585) administration was just 5%. This is despite the fact that all doses of BI135585 from 5 mg to 200 mg evaluated in the study proved capable of significantly inhibiting 11β-HSD1 in the liver as demonstrated by the reduction of the urinary THF/THE (i.e. cortisol/cortisone) ratio relative to base line throughout the course of the study, i.e. at day 1 through day 14. In reviewing experience in the field, including reports on AZD4017, Freude notes that following repeat dosing "AZD4017 lost the ability to inhibit 11β-HSD1 in adipose tissue" and "that inhibition of 11β-HSD1 activity in AT [adipose tissue] after single doses (50% vs baseline) was not observed after 9 days of treatment [with AZD4017]; therefore, it could be concluded that single-dose adipose enzyme inhibition data are not predictive of a sustained inhibition after repeated dosing". As commented in both Freude and Morentin Gutierrez, these and similar findings lead to the termination of many 11β-HSD1 programmes and established a belief in the field that 11β-HSD1 inhibition in the adipose and other peripheral tissues could not be sustained on repeat dosing. To the best of our knowledge, no 11β-HSD1 inhibitor has proved capable of delivering a sustained reduction in cortisol levels in the adipose tissue following chronic dosing.

The origins of the reduced activity of 11β-HSD1 inhibitors in inhibiting cortisol production within tissues over time and the systemic environment was investigated and has been ascribed as primarily due to negative hypothalamic pituitary adrenal (HPA) axis feedback. This negative HPA axis feedback triggers an increase in the total level of 11β-HSD1 enzyme expression. Consequently, an increase in systemic cortisol and cortisone production was established to result from treatment of human patients with selective 11β-HSD1 inhibitors such as AZD4017. This negative feedback from the HPA axis delivers reduced efficacy for 11β-HSD1 inhibitors on prolonged dosing, casting serious doubt as to their therapeutic potential for chronic conditions, particularly those in peripheral tissues such as the skin. In addition, although in previous clinical studies a reduction in the ratio of urinary metabolites of cortisone and cortisol (THF/THE ratio) has been measured and sustained, this reduction has not been associated with sustained clinical benefit. To the best of our knowledge no selective 11β-HSD1 inhibitors has been approved for clinical use despite extensive studies on their utility in conditions such as type 2 diabetes.

A range of selective 11β-HSD1 inhibitors are described in the literature see e.g. J. S. Scott et al, *J Med Chem* 2014, 57, 4466-86 and include BVT-2733, BVT-14225, BVT-3496, BVT-116429, AMG-221, MK-0736, PF-915275, PF-877423, HSD-621, HSD-016, AZD6925, AZD8329, ABT-384, BMS-770767, KR-65344, SAR184841, INCB13739, RO5093151 & BI135585. To the best of our knowledge, no evidence of an effect on human wound healing resulting from 11β-HSD1 inhibitor administration has been shown prior to the results presented herein. Furthermore, based on clinical experience with 11β-HSD1 inhibitors there was an expectation that 11β-HSD1 inhibition in peripheral tissues such as the skin could not be sustained on chronic dosing due to the operation of a negative hypothalamic pituitary adrenal (HPA) axis feedback. Also, prior to the present study it had not been shown that oral administration of AZD4017 would result in sufficient concentrations of the inhibitor reaching the skin in adequate concentrations to inhibit 11β-HSD1 activity.

It is an object of the present disclosure to provide a new strategy for treating diabetic wounds as described below based on surprising results obtained in a clinical trial in diabetic patients susceptible to developing chronic wounds.

In all embodiments of the present disclosure described herein, the selective 11β-HSD1 inhibitor for use, for use in methods of treatment, or for use in the manufacture of a medicament for treatment is AZD4017, also known as (S)-2-(1-(5-(cyclohexylcarbamoyl)-6-(propylthio)pyridin-2-yl)piperidin-3-yl)acetic acid, i.e. the compound of formula (I) below. In addition, in all embodiments the administration in such uses and methods or of such medicaments is via the oral route. AZD4017 is described in WO2008/053194 wherein full details of how the compound can be synthesised are to be found. AZD4017 may be provided in a pharmaceutically acceptable salt form.

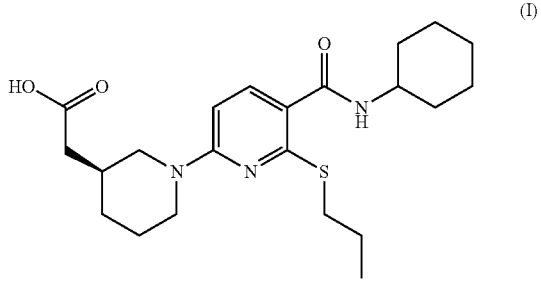 [SMILES: CCCSc1nc(N2CCC[C@@H](CC(=O)O)C2)ccc1C(=O)NC1CCCCC1]

In a first aspect the present specification provides the selective 11β-HSD1 inhibitor AZD4017, or a pharmaceutically acceptable salt thereof, for use in the treatment or prophylaxis of wounds in a patient susceptible to develop chronic wounds, for example a diabetic patient. For the avoidance of doubt, reference to wounds throughout the specification refers to skin wounds. As used herein, treatment of wounds refers to an improvement in the wound healing process relative to that expected for the patient in the untreated state, i.e. relative to an untreated patient or a patient treated with placebo. As used herein, prophylaxis of wounds refers to treatment of patients susceptible to developing chronic wounds such that if they sustain a wound the chance that the wound will develop into a chronic wound is reduced relative that expected for the patient in the untreated state, i.e. relative to an untreated patient or a patient treated with placebo. The improvement in the wound healing process will typically entail a greater degree of wound healing over a given period of time i.e. the total time for a wound to heal or an increase in the rate at which the size of the wound reduces. The improvement in the wound healing process may, in addition, be evidenced by the quality of the skin either globally, or in and around the wound site, or the quality of the healing process.

In a second aspect, the present specification provides a method of treatment or prophylaxis of wounds in a patient in need thereof, for example a patient susceptible to develop chronic wounds, comprising administering to said patient a therapeutically effective amount of AZD4017, or a pharmaceutically acceptable salt thereof. The patient in need may be a patient diagnosed with diabetes mellitus and will typically be undergoing treatment for this condition. The diabetes may be type 1 or type 2 diabetes.

In a third aspect, the present specification provides AZD4017, or a pharmaceutically acceptable salt thereof, for use in the manufacture of a medicament for the treatment or prophylaxis of wounds.

In a fourth aspect, the present specification provides a pharmaceutical composition comprising AZD4017, or a pharmaceutically acceptable salt thereof, for use in the treatment or prophylaxis of wounds. In this aspect the composition is for oral administration. In a related aspect the invention provides a method of treatment or prophylaxis of wounds in a patient in need thereof, for example a patient susceptible to develop chronic wounds, comprising administering to said patient an oral pharmaceutical composition comprising AZD4017, or a pharmaceutically acceptable salt thereof.

In a fifth aspect, the present specification provides a kit comprising an oral pharmaceutical composition comprising AZD4017, or a pharmaceutically acceptable salt thereof, and instructions for its use in the treatment or prophylaxis of wounds.

In preferred aspects described herein and above the patient in need is a human patient with diabetes mellitus, for example type 1 diabetes or type 2 diabetes. In other preferred aspects the patient is a human patient being treated with a glucocorticoid therapy, i.e. a patient being treated with a steroidal anti-inflammatory drug such as prednisolone or a human patient with an age of over 60 years, for example a patient that is 70, 75 or 80 years old.

FIGURES

So that the disclosure may be better understood, the specification refers to the following figures.

FIG. 1: Conversion of $^3$H cortisone [20 nM] to $^3$H cortisol (%/100 mg adipose tissue) after repeated dosing of AZD4017.

FIG. 2: Figure reproduced from *Br J Pharmacology* 2015, 172, 4806-4816 The plot provides a comparison of the PK/PD relationship between ex vivo activity of the human 11β-HSD1 enzyme in sub-cutaneous adipose tissue (AT) biopsies (measured as the conversion of 3H-cortisone to 3H-cortisol) and free plasma concentrations of AZD8329 both after acute and repeat oral administration (n=6 per dose level). A direct response (Emax) model was used to fit the PK/PD results. The observed results for day 1 and for day 9 are shown with the corresponding lines representing the model fit for each set of observations. Notably the enzyme activity at day 9 is greater than that observed at day 1 illustrating the reduced efficacy of the 11β-HSD1 on prolonged dosing.

Figure 3:
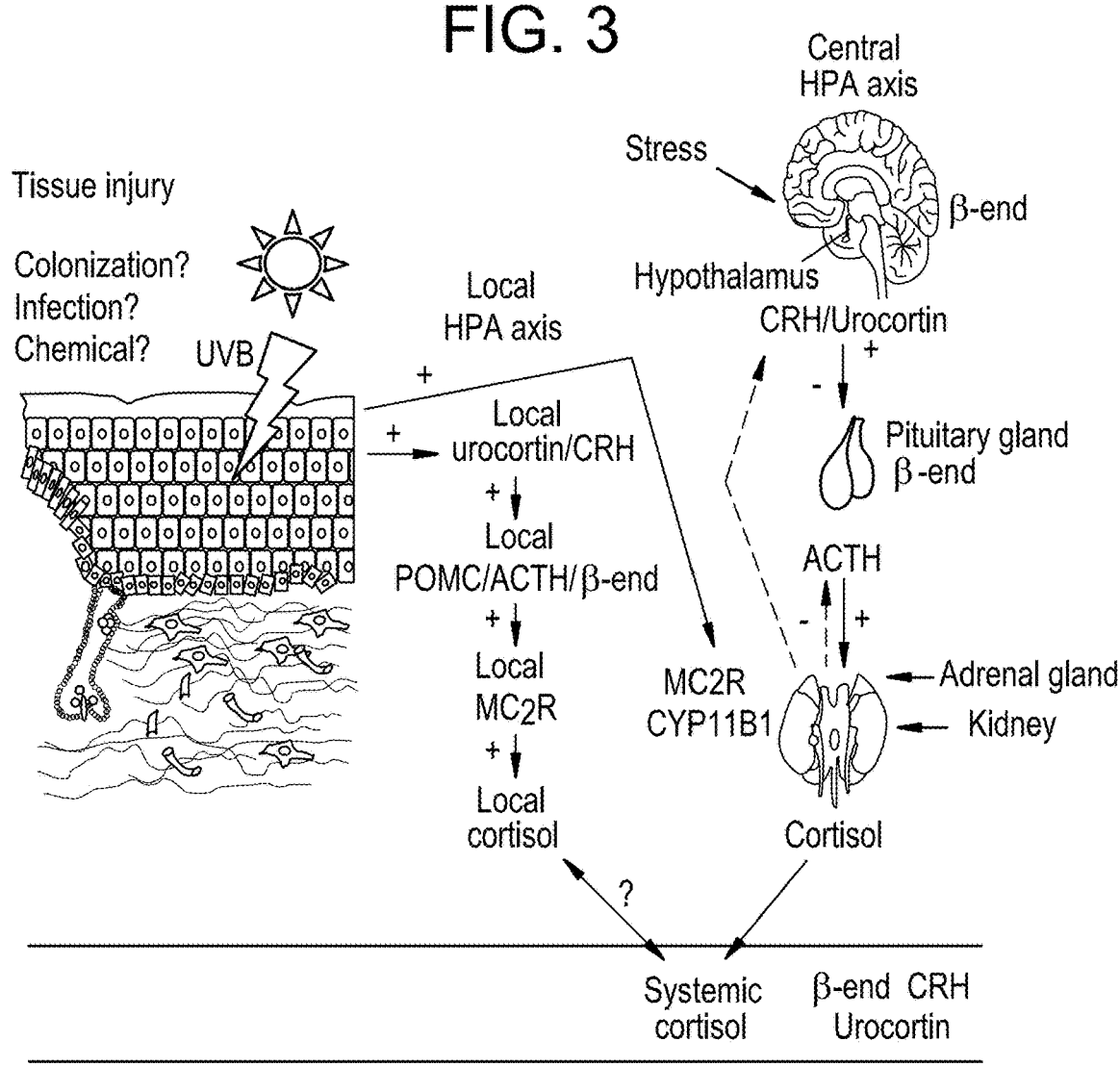

FIG. 3: Diagram from *J Invest Dermatol*: Volume 135, Issue 6, June 2015, pages 1469-1471 outlining the potential for separate mechanisms of systemic and cutaneous cortisol regulation.

Figure 4:
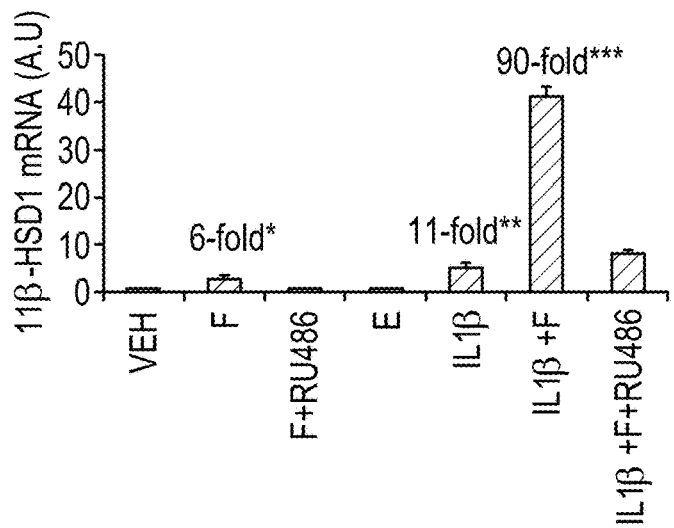

FIG. 4: Lack of regulation of GC target gene expression (e.g. 11β-HSD1) by 11β-HSD1 in primary human dermal fibroblasts. VEH: vehicle, F: cortisol, RU486: glucocorticoid receptor inhibitor, E: cortisone, IL1β: interleukin 1β (pro-inflammatory cytokine).

Figure 5:
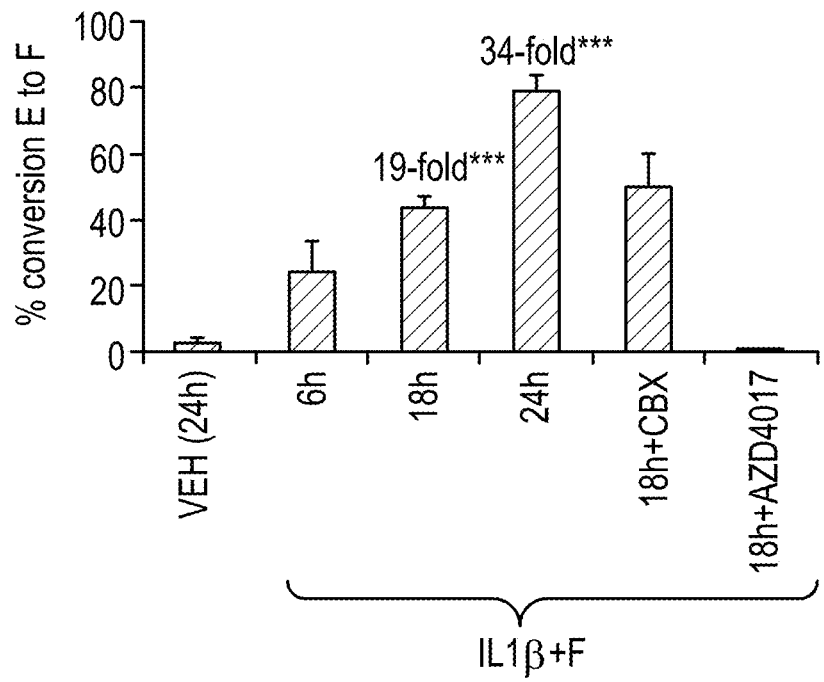

FIG. 5: 11β-HSD1 activity in primary human dermal fibroblasts. VEH: vehicle, IL1β: interleukin 1β (pro-inflammatory cytokine), F: cortisol, CBX: carbenoxolone (non-selective 11β-HSD inhibitor), AZD4017: selective 11β-HSD1 inhibitor.

Figure 6:
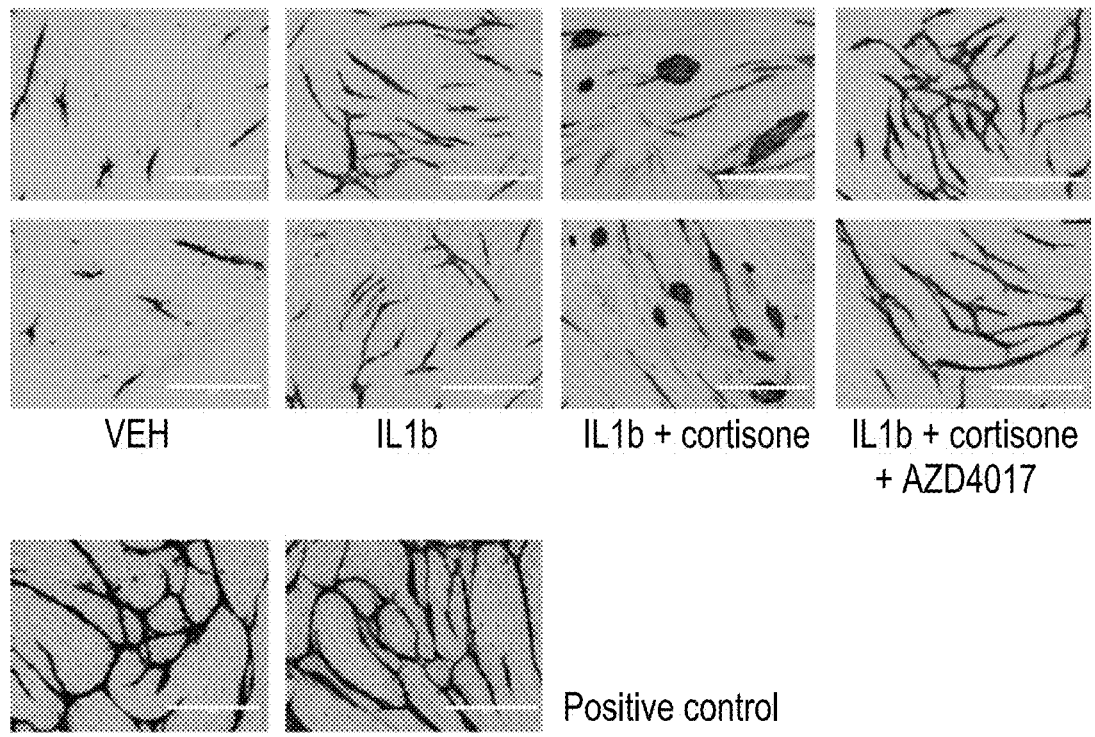

FIG. 6: 11β-HSD1-mediated regulation of HUVEC tubule formation. VEH: ethanol, IL1b: 10 ng/ml IL-1β, cortisone: 200 nM, AZD4017: 1 μM, biological n=1.

Figure 7:
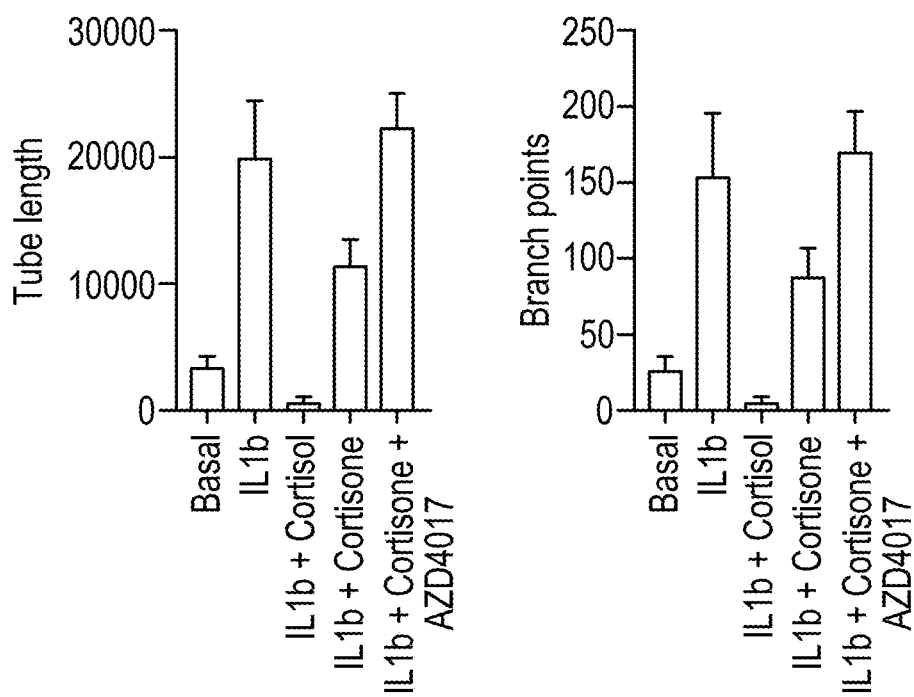
Figure 7:
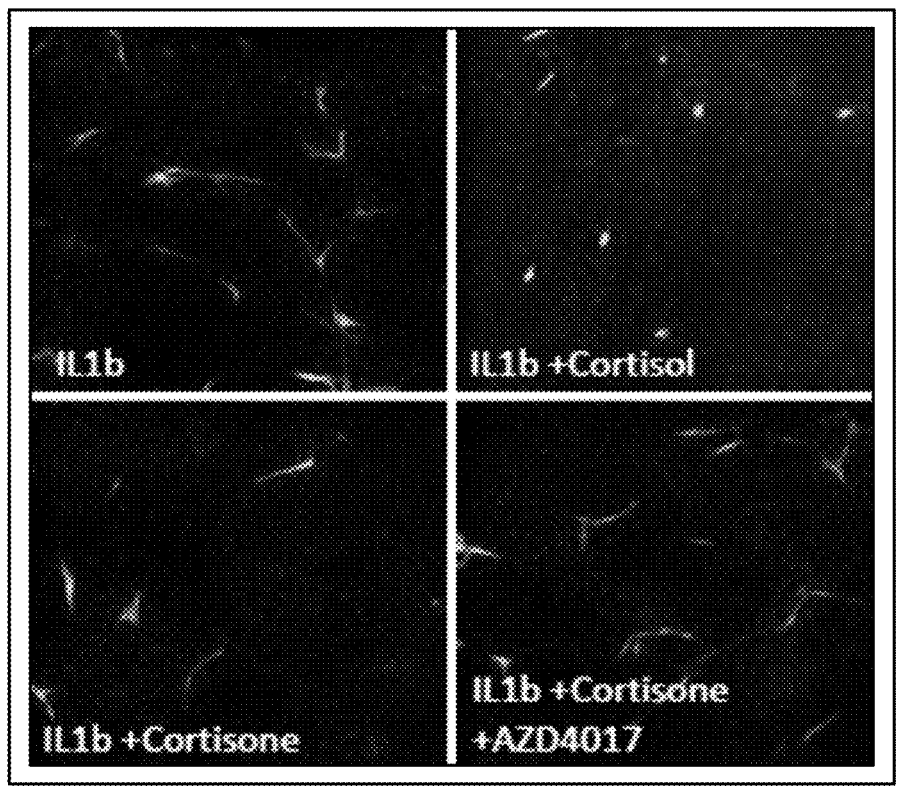

FIG. 7: AZD4017 decreased the negative effects of cortisone/cortisol on the IL-1β stimulated tube formation and thus angiogenesis.

Figure 8A:
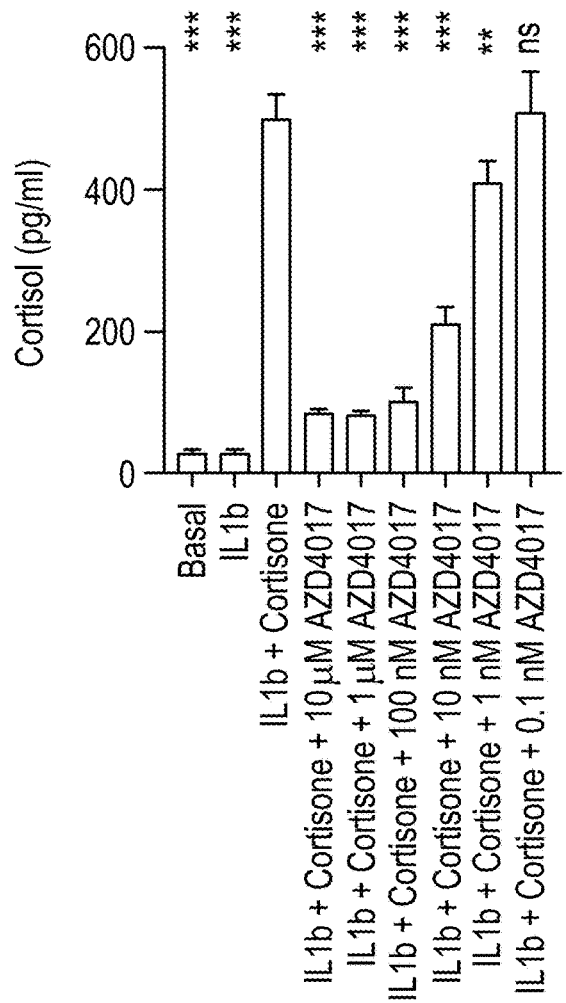
Figure 8B:
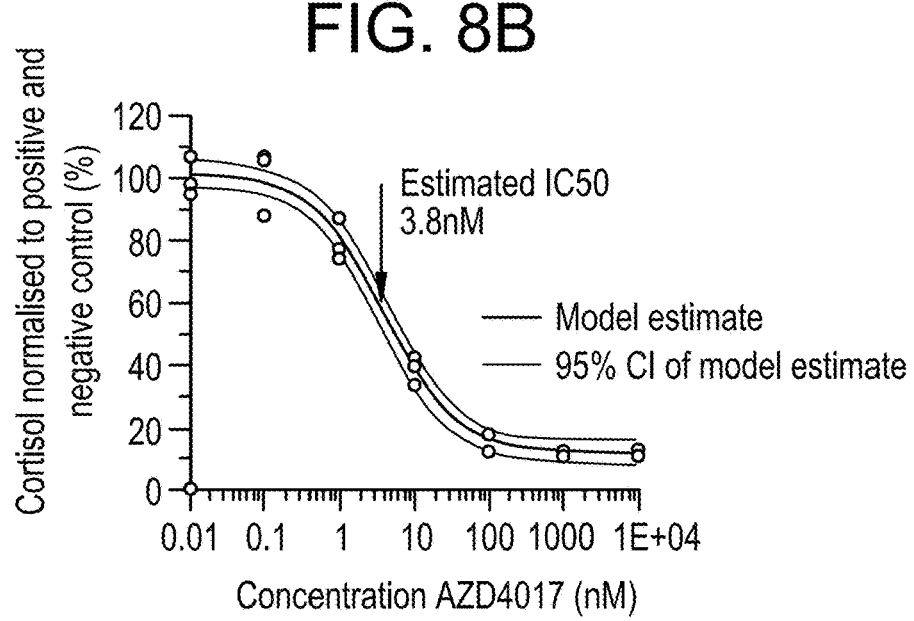

FIGS. 8*a* and 8*b*: Dose response of AZD4017 treatment on HDF cells performed with cortisol levels as readout establishes the relationship between cortisol inhibition and angiogenesis.

Figure 9:
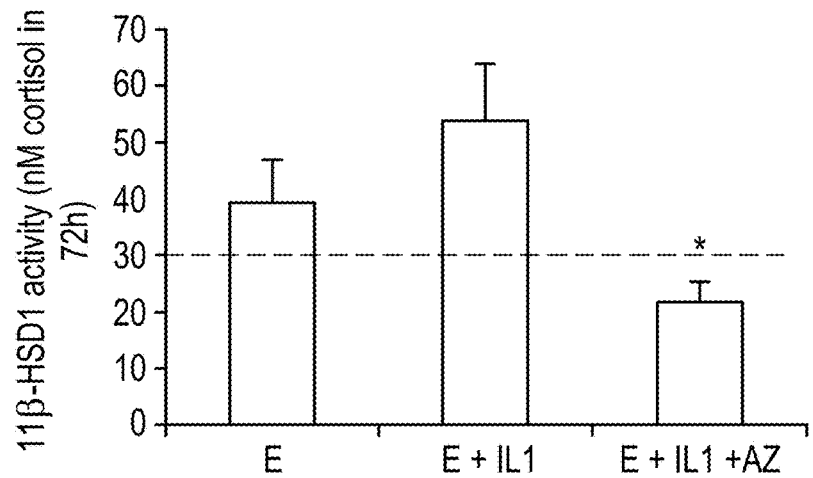

FIG. 9: 11β-HSD1 activity in 50 mg human skin (abdominal) E: 200 nM cortisone, IL1: 10 ng/ml IL-1β, AZ: 1 μM AZD4017, *=vs. cortisone+IL-1β (p<0.05), red line=threshold for GR activation, biological n=7.

Figure 10:
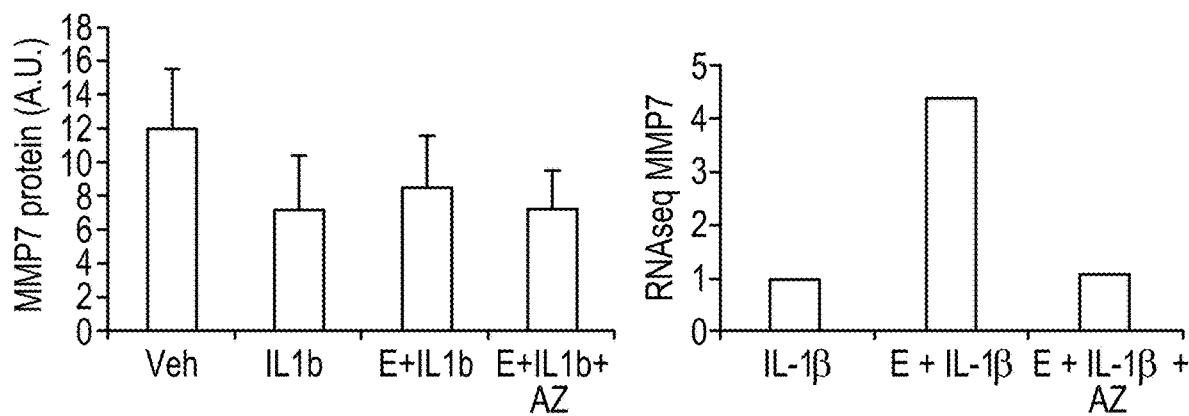

FIG. 10: Regulation of MMP7 by 11β-HSD1 MMP7 protein and gene expression displayed comparable regulation by 11β-HSD1 (n=3); AZ=AZD4017.

Figure 11:
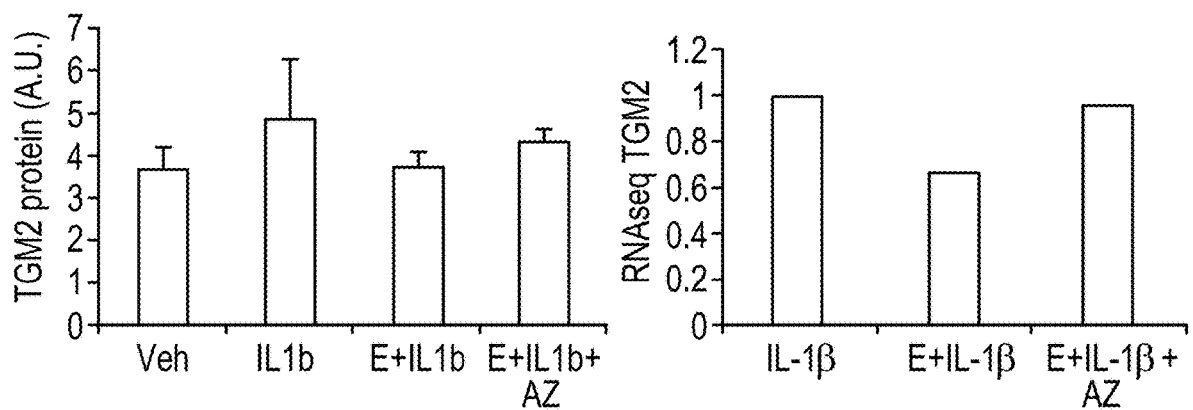

FIG. 11: Regulation of TGM2 by 11β-HSD1 TGM2 protein and gene expression displayed comparable regulation by 11β-HSD1 (n=3); AZ=AZD4017.

Figure 12:
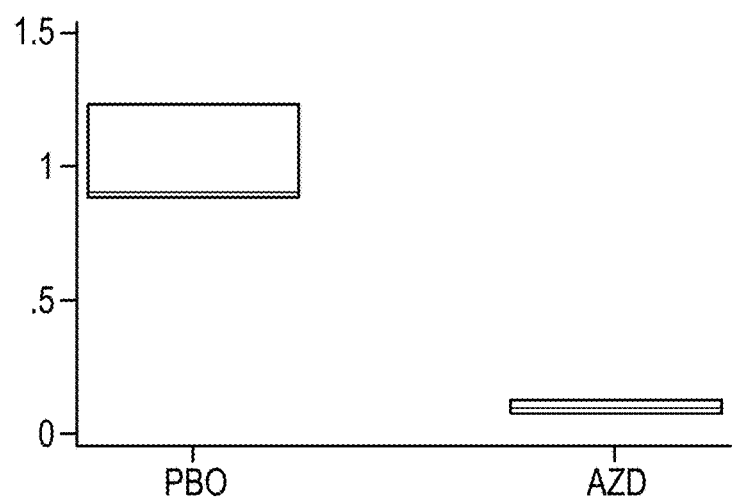

FIG. 12: Urinary [THF+alloTHF]/THE ratio at day 35 demonstrates target engagement and systemic inhibition of 11β-HSD1 by AZD4017 (AZD) relative to placebo (PBO).

Figure 13:
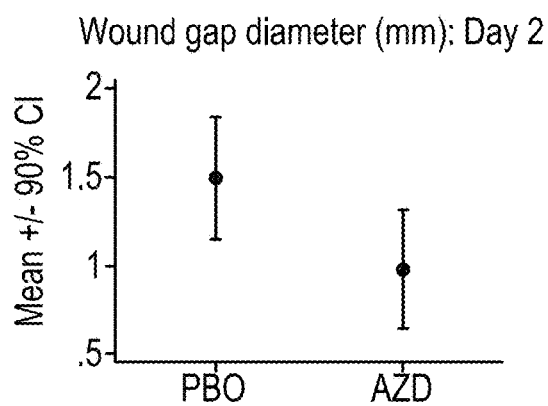
Figure 13:
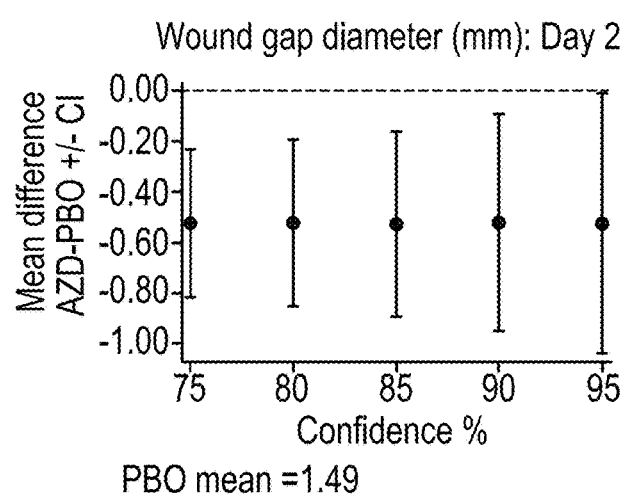
Figure 13:
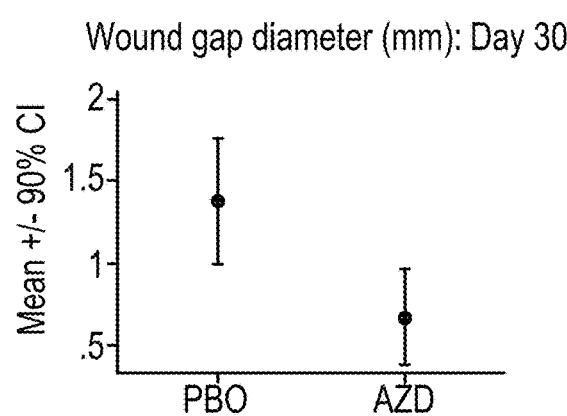
Figure 13:
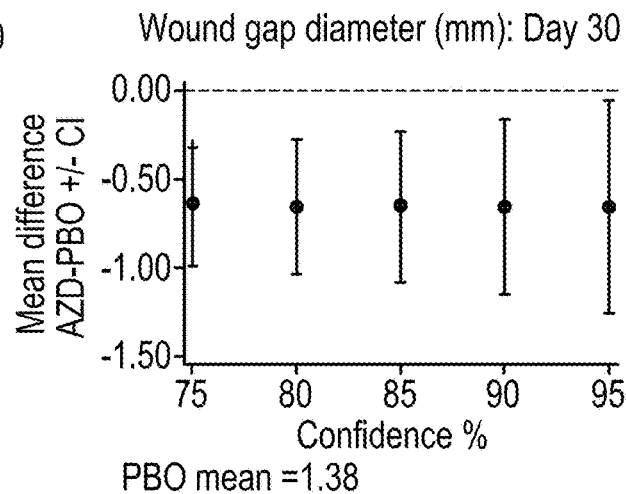

FIG. 13: Wound healing in placebo (PBO) and AZD4017 (AZD) treated cohorts as evidenced by wound gap diameter of wounds inflicted at days 0 and 28 at days 2 and 30, respectively. Confidence intervals for measurements are provided to right.

Figure 14:
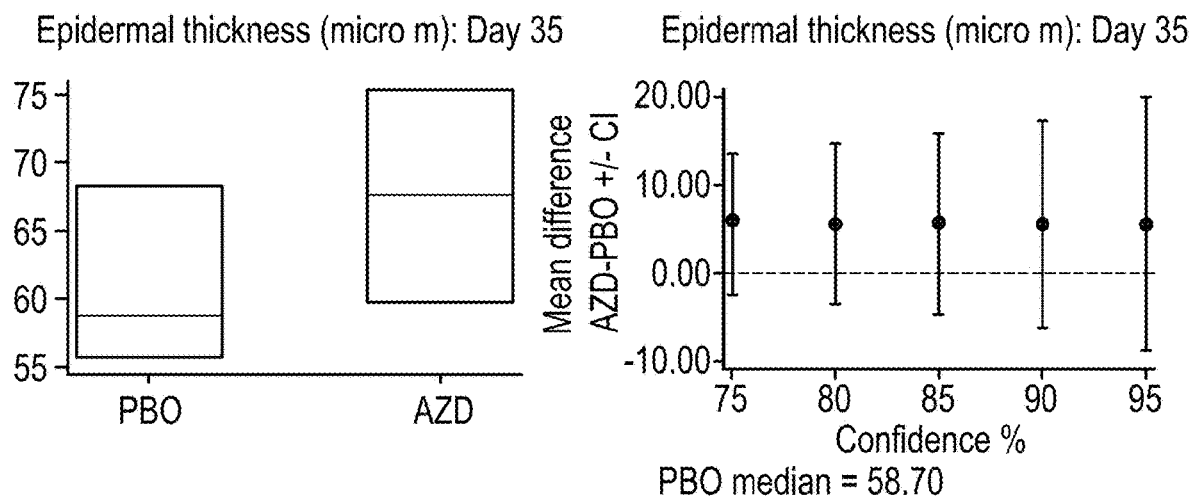

FIG. 14: Epidermal thickness (μm) in the placebo (PBO) and AZD4017 (AZD) treated arms after 35 days.

Figure 15:
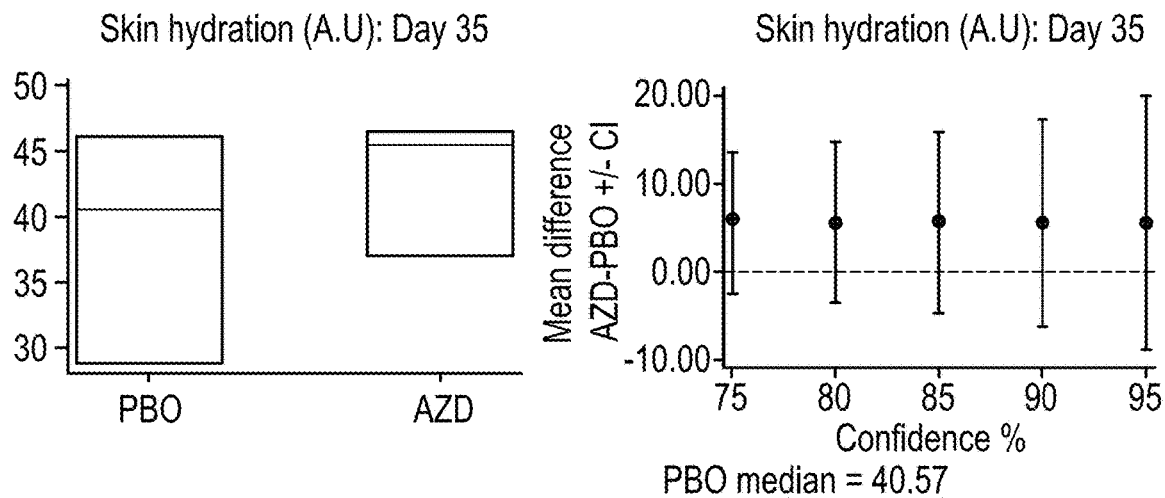

FIG. 15: Skin hydration in arbitrary units in the placebo (PBO) and AZD4017 (AZD) treated arms at 28 days as measured with a Corneometer CM 825 device.

Figure 16:
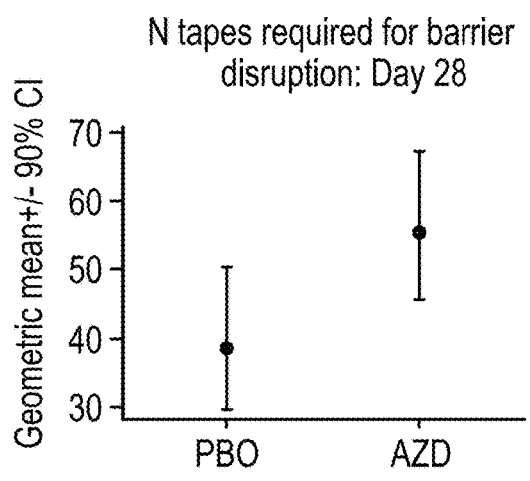
Figure 16:
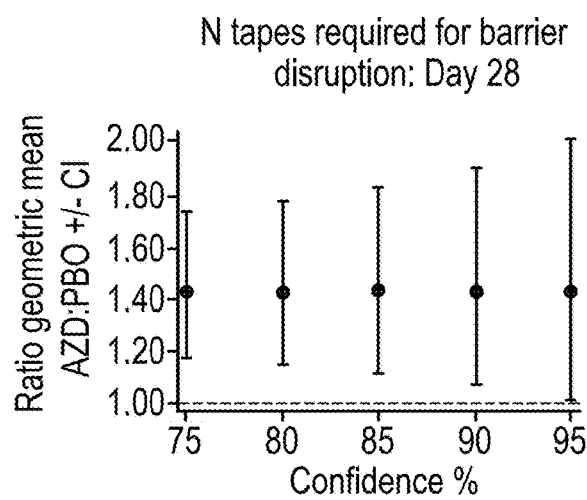

FIG. 16: The number of tapes (N tapes) required to achieve the equivalent amount of barrier disruption in the placebo (PBO) and AZD4017 (AZD) treated arms at day 28. Confidence intervals are presented to the right.

Figure 17:
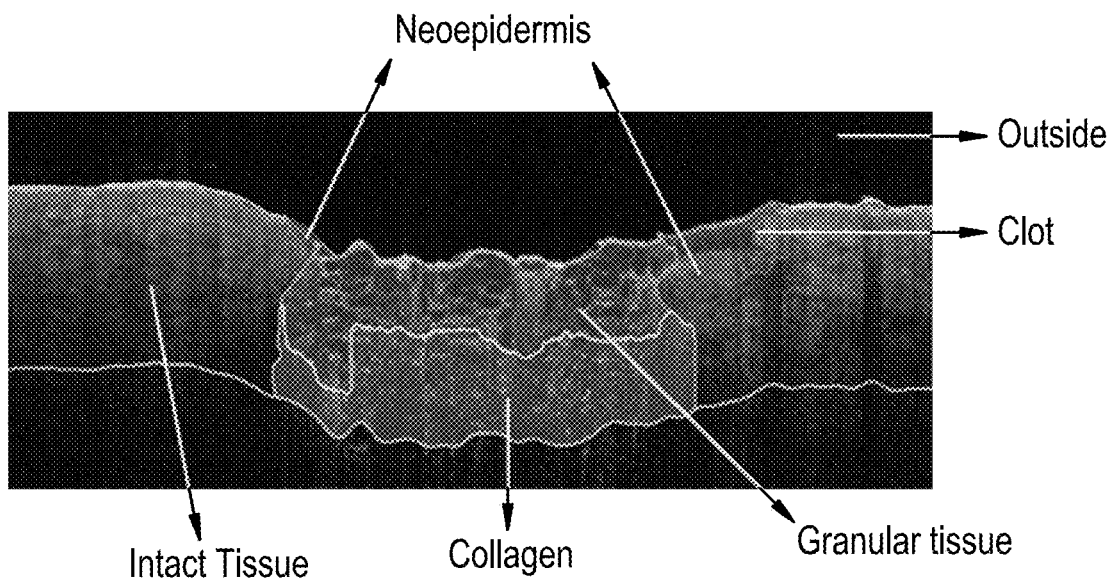

FIG. 17: 2D OCT image of wound segmented into compartments. i) void; ii) intact tissue; iii) wound collagen; iv) wound with sponginess morphology; v) neoepidermis; vi) clot & vii) blood (in liquid form).

Figure 18:
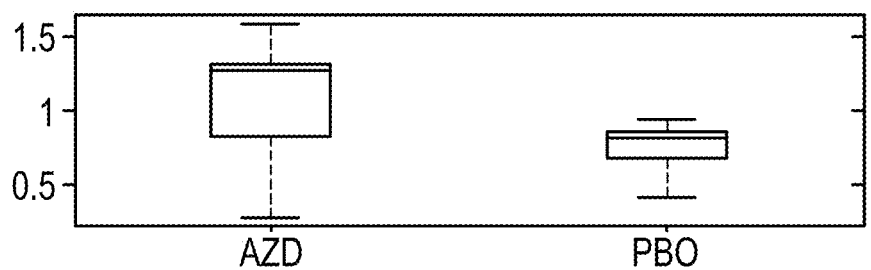
Figure 18:
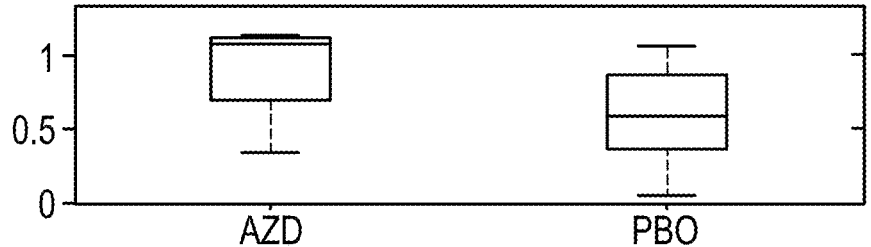

FIG. 18: Figure illustrating the improved amount of A) neoepidermis and B) clot volume two days after wounding and after 30 days of treatment with AZD4017 (AZD) and placebo (PBO).

Although 11β-HSD1 has been the subject of extensive interest as a potential target for the treatment of type 2 diabetes amongst other conditions, prior to this work there has been no data to show that inhibition of 11β-HSD1 could improve human skin quality or provide a therapeutic benefit in the treatment or prophylaxis of wounds in human patients who are susceptible to developing chronic wounds, for example diabetic patients. Indeed, as noted above, there has been a general belief based on findings from human clinical trials that inhibition of 11β-HSD1 in peripheral tissues such as the skin via oral administration of small molecule enzyme inhibitors will not be effective on chronic dosing as a negative HPA feedback effect was observed in various clinical trials investigating the therapeutic application of 11β-HSD1 inhibitors that actually resulted in increased cortisol levels in these tissues (see FIGS. 1 and 2, and comments thereon above).

In addition to the prejudice in the art against using orally administered 11β-HSD1 inhibitors to target peripheral tissues, prior to the results presented herein, it was not known that the sufficient amounts of AZD4017 could reach the skin to inhibit 11β-HSD. A key finding in the wound healing study described herein is that for the first time AZD4017 exposure within the cutaneous environment in humans following oral dosing has been demonstrated. Pharmacokinetic data demonstrating AZD4017 exposure within skin biopsy samples above the required concentration for inhibition of 11β-HSD1 are presented herein.

Furthermore, contrary to the previous clinical experience with AZD4017 (and other clinically evaluated selective 11β-HSD1 inhibitors), AZD4017 has been found in the present study to be effective in inhibiting cortisol production on prolonged administration and this has been shown to correlate with a beneficial effect on the rate of wound healing in humans that is sustained over the course of the 35 day study. Indeed, the improvement of the rate and extent of wound healing following AZD4017 treatment was not only sustained, but was actually observed to improve on prolonged exposure. As such the data reported herein demonstrates for the first time in humans the potential for operation of a cutaneous HPA axis that is regulated separately from the systemic HPA axis. Notably the negative regulation seen within the systemic HPA axis is not seen within the cutaneous environment in this study (see FIG. 3, taken from Jozic. I et al, *J Invest Dermatol*: Volume 135, Issue 6, June 2015, pages 1469-1471 for a graphic representation of a separate cutaneous HPA axis; Sjöstrand M, Hansson G I, Hartford M et al. Pharmacodynamic effects of AZD4017, a selective 11beta-HSD1 inhibitor, in liver and adipose tissue (Abstract 1161-P). *Diabetes* 2011; 60: A319). It therefore appears from the results of the present study that the primary source of cortisol production in the cutaneous environment is from the conversion of cortisone to cortisol by the enzyme 11β-HSD1. The finding that AZD4017 reaches the skin in sufficient concentrations to inhibit 11β-HSD1 and that in the skin prolonged exposure to AZD4017 does not appear to induce fresh enzyme that would negate the effect of inhibitor administration provides for the first time an opportunity to treat patients susceptible to the development of chronic wounds with the selective 11β-HSD1 inhibitor AZD4017. A hitherto unrealised opportunity for the treatment and prophylaxis of human patients susceptible to developing chronic wounds involving administration of AZD4017 is thus established based on the unprecedented ability of AZD4017 to improve skin quality thus making the skin more resistant to wounding and its ability to promote healing if wounds are sustained. Accordingly the specification provides for the use of AZD4017 in the treatment or prophylaxis of wounds wherein the orally administered AZD4017 is for chronic dosing, i.e. for dosing for a period of two weeks or more. Optionally the dosing of AZD4017 is at a dose of 400 mg twice daily.

The results of the clinical trial presented herein for the first time show, surprisingly, that administration of AZD4017 can improve the rate of wound healing in human diabetic patients and, additionally, that the skin quality of patients, as determined by measurement of parameters such as mechanical resilience, hydration and epidermal thickness is improved, thus providing a new opportunity for the treatment or prophylaxis of patients at an elevated risk of developing chronic wounds. Improvements in skin quality and properties as a result of treatment with AZD4017, for example an increase in parameters such as skin hydration and epidermal thickness, suggest that AZD4017 treatment may be used prophylactically to protect against the development of wounds as well as for the promotion of wound healing. Adverse side-effects of glucocorticoid use include skin thinning, dermal atrophy, impaired wound healing and increased infection risk. Results presented herein support the application of AZD4017 for use in the treatment or prophylaxis of patients susceptible to development of chronic wounds by virtue of their treatment with corticosteroids. Reduced skin hydration also favours development of wounds as dry skin is susceptible to cracking. Reduced skin hydration (i.e. dry skin) is common in the elderly and the elderly, as a group, are consequently predisposed to develop chronic wounds. Based on the results described herein, AZD4017 has potential for use in the treatment or prophylaxis of wounds in elderly patients, for example those presenting with dry skin.

Development of wounds is particularly significant in diabetic patients, since such patients have a propensity to develop chronic wounds to the foot, or diabetic foot ulcers. Diabetic foot wounds can be categorised on the University of Texas diabetic wound classification system (Armstrong et al, *Diabetes Care* 1998; 21:855) and can lead to amputation, and even death, if complications arise. Criteria for the categorisation of the risk of developing a diabetic foot problem or needing an amputation are provided in the NICE Guidelines NG19 (Diabetic foot problems: prevention and management NICE guideline Published: 26 Aug. 2015 www.nice.org.uk/guidance/ng19). The NICE criteria for categorisation are based on an examination of a patient's foot for neuropathy, limb ischaemia, ulceration, callus, infection and/or inflammation, deformity, gangrene and Charcot arthropathy (see NG19 section 1.3.4). High risk patients are those who have suffered a) previous ulceration or b) previous amputation or c) on renal replacement therapy or d) neuropathy and non-critical limb ischaemia together or e) neuropathy in combination with callus and/or deformity or f) non-critical limb ischaemia in combination with callus and/or deformity. Patients with an active diabetic foot problem are defined as those with ulceration, spreading infection, critical limb ischaemia, gangrene, suspicion of an acute Charcot arthropathy, or an unexplained hot, red, swollen foot with, or without, pain. The NICE Guideline NG19 recommends that patients at high risk are evaluated very frequently—up to weekly evaluation is recommended at 1.3.11.

At present medical management of diabetic foot problems revolves around good foot care to prevent wounding and, in active cases, management of infection and related pathologies (e.g. ischaemia). There is therefore a clear medical need for prophylactic agents that can protect against the development of chronic wounds, especially chronic foot ulcers. Prophylactic agents would ideally also promote healing of extant or fresh wounds. Advantageously, any such agent would greatly reduce the clinical burden and cost of managing patients prone to developing chronic wounds such as diabetic patients.

As described herein the present study has revealed that AZD4017 administered orally to diabetic patients can deliver improvements in skin quality as evidenced by improved skin moisture (this protects against wound development associated with dry skin), increased epidermal thickness (an increased barrier layer will protect against wound development and severity) and increased mechanical integrity of the skin of patients following AZD4017 treatment. These positive improvements on skin quality are delivered in addition to an improvement in the rate and extent of wound closure observed in the study. AZD4017 is thus indicated for prophylactic use, as well as for use in an interventional therapeutic context, for diabetic patients identified as being at moderate or high risk of developing diabetic foot problems as a whole or chronic diabetic foot ulcers per se. Patients at risk can be identified by the criteria of Guideline NG19 (see above). For example, patients who have already suffered from a prior foot ulcer are indicated for treatment or prophylaxis with AZD4017.

Accordingly, the present specification provides AZD4017, or a pharmaceutically acceptable salt thereof, for use in the treatment or prophylaxis of wounds, wherein AZD4017 is administered orally.

According to a further embodiment, there is provided AZD4017, or a pharmaceutically acceptable salt thereof, for use as an oral agent for the treatment of wounds.

According to a further embodiment, there is provided AZD4017, or a pharmaceutically acceptable salt thereof, for use as an oral agent for the prophylaxis of wounds.

In such embodiments the use of AZD4017 may provide an improvement in the rate of wound closure, for example a rate of wound closure at least 10% greater than that obtained with placebo. In such embodiments the use of AZD4017 may provide an improvement in epidermal thickness relative to that measured prior to treatment. In such embodiments the use of AZD4017 may provide an improvement in skin hydration relative to that measured prior to treatment. In such embodiments the use of AZD4017 may provide a thickening of the stratum corneum relative to that measured prior to treatment. In such embodiments the use of AZD4017 may provide a strengthening of the corneal layer relative to that measured prior to treatment, for example as measured by the N tapes method described herein.

The use will typically be in patients who are susceptible to develop chronic wounds, for example patients with type 1 or type 2 diabetes, elderly patients (i.e. patients over 60 years old, for example patients over 70, 75 or 80 years old) or patients undergoing therapy with a glucocorticoid such as prednisolone. In such embodiments the AZD4017 may be orally administered at a dose of 400 mg twice daily for a period of at least two weeks, for example one, two or three months or more.

According to a further embodiment, there is provided AZD4017, or a pharmaceutically acceptable salt thereof, for oral use in the treatment or prophylaxis of wounds in a diabetic patient, for example a patient with type 1 or type 2 diabetes. In such embodiments the AZD4017 may be orally administered at a dose of 400 mg twice daily for a period of at least two weeks, for example one, two or three months or more.

According to a further embodiment, there is provided AZD4017, or a pharmaceutically acceptable salt thereof, for oral use in the treatment of wounds in a diabetic patient, for example a patient with type 1 or type 2 diabetes. In such embodiments the AZD4017 may be orally administered at a dose of 400 mg twice daily for a period of at least two weeks, for example one, two or three months or more.

According to a further embodiment, there is provided AZD4017, or a pharmaceutically acceptable salt thereof, for oral use in the prophylaxis of wounds in a diabetic patient, for example a patient with type 1 or type 2 diabetes. In such embodiments the AZD4017 may be orally administered at a dose of 400 mg twice daily for a period of at least two weeks, for example one, two or three months or more.

In embodiments AZD4017, or a pharmaceutically acceptable salt thereof, is provided for oral use in the treatment or prophylaxis of wounds in a diabetic patient, for example a patient with type 1 or type 2 diabetes. In such embodiments, the patient may be a patient that has been identified as being at moderate or high risk of developing a diabetic foot problem according to the NICE Guidance NG19. For example, as detailed above, the identification of the patient as at high risk may have been made on the basis that the patient a) has or previously has had ulceration or b) has had a previous amputation or c) has had renal replacement therapy or d) exhibits neuropathy and non-critical limb ischaemia together or e) exhibits neuropathy in combination with callus and/or deformity or f) exhibits non-critical limb ischaemia in combination with callus and/or deformity.

In embodiments there is provided AZD4017 for use in the promotion of angiogenesis at a wound site in the skin following wounding. In such embodiments the promotion of angiogenesis at the wound site will lead to an increase in the rate of wound healing, for example as demonstrated by an increase in the rate of wound closure.

According to a further embodiment, there is provided AZD4017, or a pharmaceutically acceptable salt thereof, for use in the manufacture of an oral medicament for use in the treatment or prophylaxis of wounds. In such embodiments the medicament may be indicated for use in diabetic patients, i.e. patients with type 1 or type 2 diabetes. In such embodiments, the patient may be a patient that has been identified as being at moderate or high risk of developing a diabetic foot problem according to the NICE Guidance NG19. For example, as detailed above, the identification of the patient as at high risk may have been made on the basis that the patient a) has or previously has had ulceration or b) has had a previous amputation or c) has had renal replacement therapy or d) exhibits neuropathy and non-critical limb ischaemia together or e) exhibits neuropathy in combination with callus and/or deformity or f) exhibits non-critical limb ischaemia in combination with callus and/or deformity. Alternatively, the medicament may be indicated for use in an elderly patient, i.e. patients over the age of 60 years (for example over 70, 75 or 80 years old), or for use in a patient undergoing treatment with a glucocorticoid such as prednisolone.

The specification also provides a method of treatment or prophylaxis of wounds comprising oral administration of an effective amount of AZD4017 to a patient in need thereof. In such embodiments the patient in need thereof may be a diabetic patient, i.e. a patient with type 1 or type 2 diabetes. In such embodiments, the patient may be a patient that has been identified as being at moderate or high risk of developing a diabetic foot problem according to the NICE Guidance NG19. For example, as detailed above, the identification of the patient as at high risk may have been made on the basis that the patient a) has or previously has had ulceration or b) has had a previous amputation or c) has had renal replacement therapy or d) exhibits neuropathy and non-critical limb ischaemia together or e) exhibits neuropathy in combination with callus and/or deformity or f) exhibits non-critical limb ischaemia in combination with callus and/or deformity. Alternatively, the patient may be an elderly patient, i.e. a patient over the age of 60 years (for example over 70, 75 or 80 years old), or a patient being treated with glucocorticoids.

According to embodiments of the specification the compound for use, compound for use in manufacture of a medicament or method of treatment or prophylaxis is directed towards providing a treatment for, or prophylaxis of, wounds in patients susceptible to developing chronic wounds. The treatment or prophylaxis of wounds may also deliver further improvements in skin quality. In embodiments above and herein the compound for use, compound for use in manufacture of a medicament or method of treatment may, in addition to the effect on wounds, additionally provide an improvement in one or more of the following parameters: skin hydration, epidermal thickness or resilience of the skin to damage. Resilience of the skin to damage or developing wounds can be assessed by using a tape stripping procedure as described herein or any other suitable technique. In embodiments above and herein the compound for use, compound for use in manufacture of a medicament or method of treatment may provide an improvement in the rate of wound healing/closure of at least >10%, >20%, >30% or >50% (all relative to placebo).

In the embodiments of the present specification the compound for use, compound for use in manufacture of a medicament or method of treatment is directed towards oral dosing of AZD4017, for example in an oral dose of AZD4017 of 400 mg for administration twice daily (wherein the dose amount is the free base, or in the case of a pharmaceutically acceptable salt, a dose providing the equivalent to 400 mg of free base). The oral dose may be provided in a single dose or as a divided dose, for example as a single 400 mg dose unit or as two 200 mg dose units. Other dose amounts or dose schedules may be adopted towards the same therapeutic endpoint. In such embodiments the AZD4017 may be administered as a tablet. In embodiments the tablets of AZD4017 may comprise micronized AZD4017, microcrystalline cellulose, croscarmellose sodium, hydroxypropylcellulose, mannitol and sodium stearyl fumarate. Surprisingly, administration of such tablets on a twice daily basis at a dose of 400 mg has been shown to deliver sustained concentrations of AZD4017 in the skin of human patients in excess of the amount required to cause over 50% inhibition of 11β HSD1.

In the embodiments of the present specification the compound for use, compound for use in manufacture of a medicament or method of treatment, in addition to their benefit on the treatment or prophylaxis of wounds also provides an improvement in skin quality. The improvement in skin quality may be measured by skin moisture levels, epidermal thickness, mechanical resilience or any other suitable method.

In embodiments, the present specification provides a pharmaceutical composition comprising AZD4017, or a pharmaceutically acceptable salt thereof and at least one pharmaceutically acceptable excipient for use in the treatment or prophylaxis of wounds. The composition is for oral administration, for example a tablet or capsule composition.

In embodiments, the present specification provides a kit comprising a pharmaceutical composition comprising AZD4017 and instructions for its use in the treatment or prophylaxis of wounds. In such embodiment the AZD4017 is provided as a pharmaceutical composition for oral administration.

A range of preclinical experiments were performed to establish the effects of AZD4017 in models relevant to human wound healing and to interrogate mechanisms of relevance to the wound healing process. Some selected highlights of the results obtained in such studies are detailed herein, albeit confirmation of the potential of AZD4017 for use in the treatment of prophylaxis of wounds crystallised in the clinical results described herein.

In order to investigate the effects, prevalence and relevance of 11β-HSD1 in human skin and diabetic wound healing the effects of the proinflammatory cytokine, IL-1β on human dermal fibroblasts (HDFs) in culture was assessed in the preclinical setting. Interleukin IL-1β has been shown to have a role in a proinflammatory positive feedback loop that sustains the proinflammatory macrophage phenotype observed in poorly healing wounds of both humans and mice and that blocks the induction of a healing-associated macrophage phenotype observed during normal healing. Cortisol (also referred to herein as F), the product of the 11β-HSD1 mediated reduction of cortisone (also referred to herein as E), has been found to regulate 11β-HSD1 in a forward feedback manner with 6-fold increase in 11β-HSD1 mRNA expression in human dermal fibroblasts in vitro being observed when HDFs in culture were exposed to cortisol for 24 h. Exposure of HDFs to 10 ng/mL IL-1β stimulated a 10-fold increase in 11β-HSD1 mRNA expression in the cultured cells, while culturing HDFs with 10 ng/mL IL-1β and 100 nM cortisol provoked a 90-fold increase in 11β-HSD1 mRNA expression (see FIG. 4). These results suggest that significant levels of 11β-HSD1 could be induced in human skin at the wound site of diabetic patients by the combination of GCs and inflammatory cytokines. The IL-1β stimulated increase in 11β-HSD1 mRNA expression in HDFs was found to translate to increased 11β-HSD1 activity in these cells, with 24 h IL-1β pretreatment inducing a 6-fold increase in conversion of cortisone (E) to cortisol (F) over 48 h relative to untreated HDFs. The proinflammatory cytokine IL-1β was therefore found to induce 11β-HSD1 enzyme in human dermal fibroblasts that in turn leads to significant increase in cortisol in the skin. In these experiments RU486 (mifepristone) was used as a competitive cortisol antagonist.

Conversion of E to F in HDFs subjected to 24 h pretreatment with 24 h IL-1β and cortisol was observed to progressively increase over time, reaching a 34-fold increase in conversion of E to F (delivering >80% conversion of E to F after 24 h (see FIG. 5)). Addition of the selective 11β-HSD1 inhibitor AZD4017 (at 1 μM) to this system completely blocked the enzyme activity and, consequently, production of F (cortisol) over 18 h. In contrast the non-selective 11β-HSD1 inhibitor carbenoxolone (CBX at 25 μM) did not significantly inhibit of conversion of E to F at the same timepoint. Selective inhibition of 11β-HSD1 in HDFs thus provides a means to prevent conversion of cortisone to cortisol that is not possible with non-selective inhibitors such as carbenoxolone and provided support to the hypothesis that 11β-HSD1 might offer a means to control the concentration of cortisol in the skin, thereby promoting wound healing that would otherwise be impaired by elevated cortisol levels.

Glucocorticoids are known to inhibit angiogenesis, a key process in wound healing. To establish whether AZD4017 might have significance in this aspect of wound healing the ability of HDF factors to regulate angiogenesis through 11β-HSD1 was investigated in an in vitro model of angiogenesis. In this model system IL-1β was found to stimulate tubule formation (the equivalent of angiogenesis in this model). The IL-1β stimulated tubule formation was blocked by cortisone (200 nM) (see FIG. 6). In contrast, addition of the selective 11β-HSD1 inhibitor AZD4017 (1 μM) in combination with cortisone delivered the same IL-1β stimulated tubule formation as observed in the absence of cortisone. It would thus appear that cortisol generated via 11β-HSD1 reduction of cortisone, and thus 11β-HSD1 enzyme activity itself, negatively regulates angiogenesis. Notably this negative regulation of angiogenesis by 11β-HSD1 enzyme activity can be reversed by AZD4017. As angiogenesis is a key factor in wound healing, these results support the use of AZD4017 for the treatment or prophylaxis of wounds, for example in patients prone to develop chronic wounds. Interestingly, FNF2, VEGFA, VEGFC and HBEGF mRNA expression identified by a RNAsequencing analysis (not described herein) were all seen to be induced by IL-1β and suppressed by GC—further supporting the postulate that 11β-HSD1 through conversion of cortisone to cortisol can suppress angiogenesis in vitro. This experiment provided for the first time an indication that 11β-HSD1 could play a role in the regulation of angiogenesis.

In order to further study the effects of AZD4017 on angiogenesis in a quantitative manner, a further related experiment to that described above was performed. In this model in vitro cultured human dermal fibroblasts were treated with a) 10 ng/ml IL-1β, b) IL-1β+100 nM cortisol, c) IL-1β+200 nM cortisone or d) IL-1β+cortisone+1 μM AZD4017 (selective 11β-HSD1 inhibitor). The conditioned media from these cultures were then collected and used to stimulate angiogenesis in a mixture of fibroblasts and endothelial cell (ZHA-4000-24, obtained from CellWorks—caltagmedsystems.co.uk, this assay was performed according to the suppliers protocol (https://www.caltagmedsystems.co.uk/downloads/Kit %20Protocol %20Angiogenesis %20Co-culture%20Assay %20(ZHA-4100-24)%20Rev3, %202019-10.pdf). Angiogenesis was quantified as tube length and number of branch points after 7 days in culture.

As can be seen from FIG. 7 the presence of AZD4017 decreased the negative effects of cortisone/cortisol on the IL-1β stimulated tube formation and thus angiogenesis.

A dose response of AZD4017 treatment on HDF cells was performed with cortisol levels as readout to establish the relationship between cortisol inhibition and angiogenesis (quantified using the EIAHCOR ELISA, InVitrogen, ThermoFisher.com). AZD4017 treatment gave a cortisol $IC_{50}$ of 3.8 nM in this model, therefore demonstrating the correlation between cortisol inhibition with AZD4017 and promotion of angiogenesis. FIGS. 8A and 8B. Further evidence of the potential utility of AZD4017 in wound healing was obtained from a full thickness human skin explant (abdominal) model (explants were sourced from a non-diabetic donor). In this model IL-1β and cortisone (E), as in HDFs, were once more found to induce 11β-HSD1 activity as measured by the generation of cortisol. The IL-1β and cortisone (E) induction of 11β-HSD1 activity was successfully inhibited by coadministration with the selective inhibitor of 11β-HSD1, AZD4017 (see FIG. 9).

Protein profiling (Sciomics) conducted on primary human dermal fibroblasts (HDF) treated with vehicle, IL-1β, IL-1β+cortisone or IL-1β+cortisone+the selective 11β HSD1 inhibitor AZD4017 (n=3, same HDF as for RNAseq experiments) identified a number of proteins regulated by 11β-HSD1. Seventy of the 850 proteins showed evidence of regulation by 11β-HSD1, including 9 proteins for which regulation of gene expression by 11β-HSD1 was also detected using an RNA sequencing approach, although only 11% of 11β-HSD1-regulated RNAseq genes were represented on the protein array (70/611 genes). The proteins found to be regulated by 11β-HSD1 include MMP7 and TGM2. 11β-HSD1 inhibition downregulated MMP7 in skin (i.e HDFs, see FIG. 10), an interesting observation as MMP7 has previously been associated with impaired wound healing. Regulation of MMP7 by GC has to the best of our knowledge not previously been reported (Velasco, J., et al., *J Biol Chem*, 2011. 286(29): p. 26016-27). The transglutaminase TGM2 was seen to be downregulated by GC in this study (see FIG. 11), with 11β-HSD1 inhibition conversely proving to stimulate TGM2 protein and gene expression. TGM2 has previously been shown to promote angiogenesis during rat skin wound healing (Haroon, Z. A., et al., FASEB J, 1999. 13(13): p. 1787-95) and has also been associated with improved wound healing in diabetic mice (Galeano, M., et al., Wound Repair Regen, 2008. 16(2): p. 208-17).

Based on the promising preclinical data described above, a double-blind, randomized, parallel group, placebo-controlled phase II pilot trial investigating efficacy, safety and feasibility of 11β-hydroxysteroid dehydrogenase type 1 inhibition by AZD4017 to improve skin function and wound healing in patients with type 2 diabetes (T2DM) was performed (ClinicalTrials.gov Identifier: NCT03313297).

This study involved oral twice daily administration of AZD4017 (400 mg per dose, n=14) or placebo (n=14) in human patients with T2DM. Study participants attended a screening visit and at days 0, 2, 7, 28, 30, 35 (=day of cessation of dosing of the investigational medicinal product (IMP)) and a follow-up visit at day 42.

To evaluate efficacy of oral AZD4017 on 24 hour 11β-HSD1 activity in skin, 3 mm punch biopsies were obtained at Visits 1 (day 0) and 4 (day 28) from lower outer forearm (midpoint between wrist and elbow) performed under local anaesthetic (e.g. lidocaine). This procedure was conducted by authorised trial personnel and did not require sutures.

Efficacy

Global 11β-HSD1 Activity

Systemic 11β-HSD1 activity was inferred from urinary [THF+alloTHF]/THE ratios. These were measured in 24 hour urine samples at Visits 1 (day 0) and 6 (day 35) by liquid chromatography—mass spectrometry. Samples were taken using commercially available collection containers, frozen in aliquots and stored at −80° C. before batch shipping for analyses by the Institute of Metabolism and Systems Research (University of Birmingham) at the end of the trial. The original report generated for each sample was stored in the trial master file and recorded in the case report form (CRF) at the end of the trial. The measurement allows an examination of the associations between participant systemic GC levels and outcome measures of skin function. As can be seen from FIG. 12 the Urinary [THF+alloTHF]/THE ratio at day 35 reveal a very substantial reduction in the ratio of cortisol to cortisone (from ca 1 to <0.1) in the 11β-HSD1 inhibitor treated cohort thus demonstrating target engagement and efficacy of AZD4017 in inhibiting global 11β-HSD1 enzyme activity over the course of the trial. As noted above, inhibition of global 11β-HSD1 enzyme activity has not previously translated into sustained efficacy in peripheral tissues such as the adipose due to negative HPA axis feedback.

AZD4017 Skin PK Data

Prior to the present study it had not been established whether or not orally dosed AZD4017 could reach the skin. AZD4017 levels were thus measured in skin at baseline. Skin samples were collected at visit 4 (day 28) and stored at −80° C. in the designated storage area before batch shipping for AZD4017 pharmacokinetic analysis by York Bioanalytical Solutions Ltd after the end of the trial. Shipping contents, collection and delivery were recorded and stored in the trial master file. The skin samples were taken in the clinic at a time point between 2 to 8 hours after the morning dose of AZD4017 and were then snap frozen until required. Skin samples were thawed prior to analysis and homogenised using ceramic beads in the Fastprep-24 system (see https://www.mpbio.com/fastprep-24-5g-instrument). The protein was then precipitated from the homogenate with ammonium acetate. The resulting skin extract was analysed by liquid chromatography with tandem mass spectrometry using TurbolonSpray, in positive ion, multiple reaction mode. The amount of AZD4017 was established by correlating the peak area of treated skin samples against that obtained with reference, untreated, skin homogenate samples spiked with known concentrations of AZD4017.

The AZD4017 concentrations measured in the skin samples are presented in Table 1 below. As can be seen, skin concentration of AZD4017 in the study ranged from 440 nM to 3.3 μM as measured by a standard LCMS protocol, in all cases well above the $IC_{50}$ value for AZD4017 for inhibition of 11β HSD1.

TABLE 1

Concentration of AZD4017 in skin samples obtained from patients at visit 4 (day 28)

| Subject ID | Observed Concentration of AZD4017 (nM) |
|---|---|
| 001 | 2440 |
| 004 | 1810 |
| 006 | 876 |
| 008 | 2020 |
| 014 | 897 |
| 015 | 794 |

TABLE 1-continued

Concentration of AZD4017 in skin samples obtained from patients at visit 4 (day 28)

| Subject ID | Observed Concentration of AZD4017 (nM) |
|---|---|
| 016 | 3220 |
| 018 | 443 |
| 022 | 1520 |
| 024 | 2440 |
| 026 | 721 |
| 030 | 1570 |
| 036 | 3310 |
| 038 | 1530 |

Wound Healing

Both biopsies from visit 1 (day 0) and two biopsies from visit 4 (day 28) were imaged by OCT at Visits 2, 3, 5 and 6 as appropriate. Optical coherence tomography OCT (Greaves, N. S., et al., *Br J Dermatol*, 2014. 170(4): p. 840-50) has proven a useful tool for the evaluation of wound re-epithelialization. OCT uses light to capture sub-micrometre resolution, three-dimensional images from within biological tissue (e.g. skin). The method is based on low-coherence interferometry, typically employing near-infrared light. The use of relatively long wavelength light allows it to penetrate 1-2 mm into the tissue. In addition to wound diameter, collected images capture information on vascularization.

The procedure takes approximately 2 minutes using a small probe applied to the skin. The procedure is non-invasive and pain-free. Image files (including enrolment number, visit number and date) were stored on the OCT machine until the end of the trial, then transferred to a secure server, compiled, analysed and values for wound diameter entered into the case report form (CRF).

Results from this study of wound healing are presented in FIG. 13. The initial wounds created by puncture at days 0 and 28, respectively, were 3 mm in diameter. Treatment with AZD4017 (400 mg, twice daily oral) was initiated on day 0 and maintained for 35 days.

At day 2 the wound gap diameter in the placebo arm and AZD4017 trial arms were compared and this comparison revealed a 35% improvement in the extent of healing in the treatment arm relative to placebo arm (mean wound gap diameter of 1.49 mm in placebo arm vs 0.98 mm in AZD4017 treated arm). Thus administration of AZD4017 on the same day as the wound was inflicted delivered a significant improvement in the rate of wound healing.

This result was confirmed, and improved upon, after 4 weeks pretreatment with the AZD4017. Results obtained after the second challenge (fresh wounding by puncture at day 28) showed that after two days (at day 30) a 55% improvement in the extent of healing is seen for AZD4017 treated arm relative to placebo arm of trial (mean wound gaps placebo=1.38 mm, AZD4017=0.67 mm).

Improvements in Skin Properties

Epidermal Thickness

As noted above, glucocorticoid therapy is known to cause skin thinning and dispose patients to the development of chronic wounds. Epidermal thickness was measured by OCT at Visits 1 (day 0) and 6 (day 35, i.e. after 35 days of treatment with 400 mg AZD4017, twice daily). Results from these measurements are presented alongside the confidence interval in the measurements at day 35. As seen from the data there is a trend towards thickening of the epidermal layer in the AZD4017 treated cohort following AZD4017 treatment (FIG. 14, the AZD4017 treated arm had an epidermal depth 5.58 µm greater than the placebo arm). Although an expanded study group is required to confirm the statistical significance of this result, the trend observed in this small preliminary study augers well and suggests that treatment with AZD4017 could be protective against development of further wounds and, furthermore, that administration of the selective 11β-HSD1 inhibitor AZD4017 delivers an improvement in general skin quality.

Skin Hydration

Stratum corneum hydration was measured using a Corneometer® CM 825 device (commercially available from Courage and Khazaka Electronic GmbH, 50829 Köln, Germany). The device measures the change in the dielectric constant due to skin surface hydration changing the capacitance of a precision capacitor and can detect even slight changes in hydration (reported in arbitrary units). The measurement was taken at Visits 1 (day 0) and 6 (day 35) with a small portable probe that was applied to the skin.

Skin hydration results from these measurements (shown in FIG. 15) revealed a distinct trend towards an increase in skin hydration over the course of the trial. The significance of this observation is that glucocorticoid use is known to cause a drying of the skin and this reduction in skin hydration predisposes the skin towards cracking and development of wounds. A causative factor in wound development is therefore diminished and this augers well for prophylactic use of AZD4017 for the prevention of wounds in patients in need thereof, for example type 2 diabetes patients.

N Tapes Data

A further way in which the skin quality of patients treated with AZD4017 was evaluated involved stripping of the skin with adhesive patches to achieve a consistent damage level as established by transepidermal water loss (TEWL), a measure of the permeability of the skin barrier.

In more detail, evaporation of water from the skin occurs as part of normal skin metabolism. As barrier function is disrupted, water loss increases. The Tewameter® TM 300 probe (commercially available from Courage and Khazaka Electronic GmbH, 50829 Köln, Germany) measures the density gradient of the water evaporation from the skin by two pairs of sensors (temperature and relative humidity) inside a hollow cylinder. The open chamber measurement method is the only method to assess the TEWL continuously without influencing its microenvironment. A microprocessor analyses the values and expresses the evaporation rate in g/h/m$^2$. The procedure requires 5 min to perform, is non-invasive, pain-free and was conducted at study visits 1, 2, 3, 4, 5 and 6 (days 0, 2, 7, 28, 30 and 35).

Adhesive patches (D-Squame® tapes, from D-Squame, Clinical and Derm LLC, Dallas, Tex., www.clinicalandderm.com) were used to gently remove the stratum corneum layers to a pre-specified TEWL (trans-epidermal water loss) rate from the lower inner forearm at Visits 1 and 4. The number of adhesive strips required to afflict the same degree of damage on the stratum corneum is a measure of the resistance of the skin to damage. In the study the number of tapes required to inflict the same degree of (mild) skin damage was greater in the 11β-HSD1 inhibitor treated cohort than in placebo arm (FIG. 16). At day, after 4 weeks treatment, the number of tapes required to induce the same level of damage on the skin as evaluated by this technique was 43% higher in the 11β-HSD1 inhibitor treated cohort than in the placebo arm. This result reveals that the strength of the corneal layer, as indicated by the amount of mechanical abrasion required to inflict a wound, is improved by administration of a selective 11β-HSD1 inhibitor.

To further understand the effects of AZD4017 in the wound healing process a deep learning based image processing method was developed for recognising different sub-tissue components from optical coherence tomography (OCT) images. The method was based on a u-net convolutional neural network (see Ronneberger O., Fischer P., Brox T. (2015) U-Net: Convolutional Networks for Biomedical Image Segmentation. In: Navab N., Hornegger J., Wells W., Frangi A. (eds) Medical Image Computing and Computer-Assisted Intervention—MICCAI 2015. MICCAI 2015. Lecture Notes in Computer Science, vol 9351. Springer, Cham. https://doi.org/10.1007/978-3-319-24574-4_28). Our method takes a slice of scanned 2D OCT image (one colour channel) and performs the segmentation of an OCT image into 7 sub-tissue components, that exist in typical wound healing pathology, namely i) Outside (void); ii) Intact tissue; iii) Wound collagen; iv) Granular Tissue; v) Neoepidermis; vi) Clot; and vii) Blood (in liquid form). An example analysis image depicting the areas listed is provided as FIG. 17.

Further morphological image processing was then performed to the labelled image as post processing processes to show meaningful continuous regions of sub-tissue components. As a result, the area (mm$^2$) of each sub-tissue components could be calculated. In addition the volume (mm$^3$) of each sub-tissue components across 120 slices of tissues were also determined. With knowledge of the volume, we also able to calculate the ratio of wound tissue within a 1 mm tissue depth.

The comparison between AZD4017 (14 patients) and placebo (14 patients) treated cases indicate that in the images obtained of the wounds on day 30, that is 2 days after wounding at day 28 of the study (i.e. after 30 days treatment with AZD4017 or placebo treatment), a statistically significant difference (p<0.05) between placebo and AZD4017 treatment in the extent of neoepidermis (i.e. new skin growth into wound site), as well as in the extent of blood clotting (FIGS. 18A & B, respectively). The ratio of total wound volume [(neoepidermis+sponginess+collagen+clot)/tissue_area] also showed a statistical significant improvement for the treatment (AZD4017) arm relative to placebo arm. The positive effects of AZD4017 treatment following the wound challenge is thus confirmed by the increase in neoepidermis (i.e. skin growth into the wound site) and the extent of blood clotting in the wound.

To summarise, the machine learning analysis of the wounds revealed that treatment with AZD4017 delivered statistical significant increases in both the volume of neoepidermis and clots in the wound site compared to placebo after 30 days on treatment. These findings further support the use of AZD4017 for the treatment of wounds in diabetic patients.

Although the clinical trial was performed on a relatively small patient population and this limits the statistical significance of some of the observations, the findings described above clearly support the postulate that administration of AZD4017 delivers inhibition of 11β-HSD1 inhibition in the skin and that this is correlated with significant improvements in wound healing and skin parameters in the AZD4017 treated patient cohort. Furthermore, no significant adverse effects were observed in the treatment cohort. AD4017 is thus identified for the first time as a safe and effective agent with therapeutic and prophylactic potential for the treatment of wound healing in patient populations susceptible to the development of chronic wounds and the complications associated therewith.

Unless defined otherwise, all technical and scientific terms used herein have the same meaning as commonly understood by one of ordinary skill in the art to which this disclosure is related. For example, the *Concise Dictionary of Biomedicine and Molecular Biology*, Juo, Pei-Show, 2nd ed., 2002, CRC Press; *The Dictionary of Cell and Molecular Biology*, 3rd ed., 1999, Academic Press; and the *Oxford Dictionary of Biochemistry and Molecular Biology*, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range.

The term "pharmaceutical composition" refers to a preparation which is in such form as to permit the biological activity of the active ingredient, and which contains no additional components which are unacceptably toxic to a subject to which the composition would be administered. Such compositions can be sterile. A pharmaceutical composition according to the present specification will comprise an 11β-HSD1 inhibitor and at least one pharmaceutically acceptable excipient. The one or more pharmaceutically acceptable excipient(s) may be chosen from the group comprising fillers, binders, diluents and the like.

Terms such as "treating" or "treatment" or "to treat" or "alleviating" or "to alleviate" refer to both (1) therapeutic measures that cure, slow down, lessen symptoms of, and/or halt progression of a diagnosed pathologic condition or disorder and (2) prophylactic or preventative measures that prevent and/or slow the development of a targeted pathologic condition or disorder. Thus, those in need of treatment include those already with the disorder; those prone to have the disorder; and those in whom the disorder is to be prevented. For example, prophylactic use of AZD4017 in the patient groups susceptible to developing chronic wounds would entail treatment of such patient with a daily regime of AZD4017 as described herein in order that should wounding occur the propensity to develop chronic wounds is reduced due to the ability of AZD4017 to accelerate the rate of wound closure and also improve skin properties such as its mechanical strength, promoting a thickening of the stratum corneum, thickening the epidermal layer, strengthening the corneal layer and skin hydration that are demonstrated herein for the first time and that could not have been predicted prior to the results of the clinical trial described herein. Patient populations particular suited to prophylactic treatment with AZD4017 include diabetic patients, a group particularly prone to developing chronic wounds such as diabetic foot ulcers that often lead to serious complications as described above. In addition, patients being treated with corticosteroids that typically experience thinning of the skin have an increased propensity to develop chronic wounds. Furthermore, elderly patients, particularly those with reduced skin hydration are also prone to developing wounds and are also indicated for prophylactic treatment with AZD4017.

AZD4017 can be used alone or in combination with further therapeutic agents. Administration of the compounds of the specification can be either simultaneous or sequential. The further therapeutic agent may be selected from additional agents such as an immunomodulator, anti-inflammatories (e.g. glucocorticoids or NSAIDs), anti-allergic agents, pain relievers and combinations thereof.

The term "subject" refers to a human that is to be the recipient of a particular treatment. Typically, the terms "subject" and "patient" are used interchangeably herein in reference to a human subject.

AZD4017 or a pharmaceutically acceptable salt thereof, will normally be administered via the oral route, in the form of pharmaceutical preparations comprising the active ingredient or a pharmaceutically acceptable salt or solvate thereof, or a solvate of such a salt, in a pharmaceutically acceptable dosage form. Depending upon the disorder and patient to be treated and the route of administration, the compositions may be administered at varying doses.

The pharmaceutical formulations of AZD4017 may conveniently be administered in unit dosage form and may be prepared by any of the methods well-known in the pharmaceutical art, for example as described in Remington's Pharmaceutical Sciences, 17th ed., Mack Publishing Company, Easton, Pa., (1985).

Pharmaceutical formulations suitable for oral administration may comprise one or more physiologically compatible carriers and/or excipients and may be in solid or liquid form. Tablets and capsules may be prepared with binding agents; fillers; lubricants; and surfactants. Liquid compositions may contain conventional additives such as suspending agents; emulsifying agents; and preservatives Liquid compositions may be encapsulated in, for example, gelatin to provide a unit dosage form. Solid oral dosage forms include tablets, two-piece hard shell capsules and soft elastic gelatin (SEG) capsules. In embodiments the specification provides a formulation of AZD4017 comprising micronized AZD4017, microcrystalline cellulose, croscarmellose sodium, hydroxypropylcellulose, mannitol and sodium stearyl fumarate, optionally wherein these components are provided in the amounts specified in Table 2. These formulations have proved to have the storage stability for commercial use and the release properties required to ensure adequate bioavailability of the drug.

TABLE 2

An exemplary formulation of AZD4017 for use in the methods of treatment according to the specification.

| Components | Quantity (mg/tablet) | Quantity (% w/w) |
|---|---|---|
| AZD4017 micronised | 200.0 | 30.77 |
| Cellulose microcrystalline/ Microcrystalline cellulose | 105.8 | 16.28 |
| Croscarmellose sodium | 65.0 | 10.00 |
| Hydroxypropylcellulose | 26.0 | 4.00 |
| Mannitol powder | 246.7 | 37.95 |
| Sodium stearyl fumarate | 6.50 | 1.00 |
| Water, purified/Purified water[a] | qs | |

[a]Removed during processing.
qs Quantum satis.

The ingredients in the table were combined by standard techniques to provide tablets for administration in the clinical trial described herein. Briefly, cellulose microcrystalline, mannitol, croscarmellose sodium, hydroxypropylcellulose and AZD4017 were blended together. The powder mix was then granulated by adding the granulation liquid (water) while mixing, followed by additional wet mixing. More water was added if necessary. The wet mass was then passed through a screen, then dried in suitable drying equipment to give a dry mass. The dried mass was milled through a suitable mill (or sieved through a suitable screen) prior to final mixing. The granules were final mixed in two consecutive mixing steps with croscarmellose sodium and sodium stearyl fumarate and then compressed into tablets using a tablet press equipped with oblong punches.

The invention claimed is:

1. A method of treatment of skin wounds comprising orally administering an effective amount of (S)-2-(1-(5-(cyclohexylcarbamoyl)-6-(propylthio)pyridin-2-yl)piperidin-3-yl)acetic acid, or a pharmaceutically acceptable salt thereof, to a patient in need thereof.

2. The method according to claim 1 wherein (S)-2-(1-(5-(cyclohexylcarbamoyl)-6-(propylthio)pyridin-2-yl)piperidin-3-yl)acetic acid, or a pharmaceutically acceptable salt thereof, is administered twice daily.

3. The method according to claim 1 wherein a dose of 400 mg of (S)-2-(1-(5-(cyclohexylcarbamoyl)-6-(propylthio)pyridin-2-yl)piperidin-3-yl)acetic acid, or a pharmaceutically acceptable salt thereof, is administered twice daily.

4. The method according to claim 1, wherein the method provides an improvement in the rate of wound closure.

5. The method according to claim 1, wherein the method provides an improvement in epidermal thickness relative to that measured prior to administration.

6. The method according to claim 1, wherein the method provides an improvement in skin hydration relative to that measured prior to treatment.

7. A pharmaceutical composition for oral administration comprising (S)-2-(1-(5-(cyclohexylcarbamoyl)-6-(propylthio)pyridin-2-yl)piperidin-3-yl)acetic acid, or a pharmaceutically acceptable salt thereof, and at least one pharmaceutically acceptable excipient for use in a method of treatment of skin wounds.

8. The pharmaceutical composition according to claim 7 in the form of a tablet or capsule for oral administration.

9. The method according to claim 1 wherein the patient in need is a diabetic patient.

10. The method according to claim 1 wherein the patient in need is receiving concurrent treatment with a glucocorticoid.

11. The method according to claim 1 wherein the patient in need is over the age of 60 years old.

12. The method according to claim 4, wherein the improvement in the rate of wound closure is at least 10% greater than that obtained with placebo.

13. The method according to claim 9 wherein the diabetic patient has been identified as being at moderate or high risk of developing a diabetic foot problem or foot ulcers or as having a foot ulcer.

14. The method according to claim 13 wherein the patient is identified as being at risk of developing a diabetic foot problem on the basis of:
  a) suffering from or having previously had ulceration; or
  b) having had an amputation; or
  c) having had renal replacement therapy; or
  d) exhibiting neuropathy and non-critical limb ischaemia together; or
  e) exhibiting neuropathy in combination with callus and/or deformity; or
  f) exhibiting non-critical limb ischaemia in combination with callus and/or deformity.

15. The method according to claim 10 wherein the glucocorticoid is prednisolone.

16. The method according to claim 11 wherein the patient in need has been diagnosed as suffering dry skin, has a history of developing chronic wounds, or has been identified as having a propensity to develop chronic wounds.

* * * * *